United States Patent
Zong et al.

(10) Patent No.: US 11,047,001 B2
(45) Date of Patent: *Jun. 29, 2021

(54) METHODS OF LINEARLY AMPLIFYING WHOLE GENOME OF A SINGLE CELL

(71) Applicant: Baylor College of Medicine, Houston, TX (US)

(72) Inventors: Chenghang Zong, Houston, TX (US); Michael Gundry, Houston, TX (US); Kuanwei Sheng, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/407,032

(22) Filed: May 8, 2019

(65) Prior Publication Data

US 2019/0264271 A1 Aug. 29, 2019

Related U.S. Application Data

(63) Continuation of application No. 15/308,592, filed as application No. PCT/US2015/029311 on May 5, 2015, now Pat. No. 10,301,671.

(60) Provisional application No. 61/989,002, filed on May 6, 2014.

(51) Int. Cl.
  *C12Q 1/68* (2018.01)
  *C12Q 1/6844* (2018.01)
  *C12Q 1/6804* (2018.01)

(52) U.S. Cl.
  CPC ......... *C12Q 1/6844* (2013.01); *C12Q 1/6804* (2013.01); *C12Q 1/6846* (2013.01)

(58) Field of Classification Search
  CPC .. C12Q 1/6844; C12Q 1/6804; C12Q 1/6846; C12Q 2525/131; C12Q 2521/301; C12Q 2525/161; C12Q 2531/119; C12Q 2537/143
  See application file for complete search history.

(56) References Cited

U.S. PATENT DOCUMENTS

| 10,301,671 B2 * | 5/2019 | Zong ............... C12Q 1/6846 |
| 2003/0149535 A1 | 8/2003 | Sudo et al. |
| 2010/0105052 A1 | 4/2010 | Drmanac et al. |
| 2012/0270212 A1 * | 10/2012 | Rabinowitz .......... C12Q 1/6862 435/6.11 |
| 2014/0200146 A1 | 7/2014 | Xie et al. |
| 2014/0213485 A1 * | 7/2014 | Weissman .......... C12N 15/1096 506/26 |

FOREIGN PATENT DOCUMENTS

| WO | 199918241 A1 | 4/1999 |
| WO | 2012166425 A2 | 12/2012 |
| WO | 2014018460 A1 | 1/2014 |

OTHER PUBLICATIONS

Dean et al., "Comprehensive human genome amplification using multiple displacement amplification", Proceedings National Academy of Sciences PNAS, National Academy of Sciences, US, Apr. 16, 2002, vol. 99, No. 8, pp. 5261-5266.
Lovett, "The applications of single-cell genomics", Hum Mol Genet, Oct. 15, 2013, vol. 22, No. R1, pp. R22-R26.
Macaulay et al., "Single cell genomics: advances and future perspectives", PLOS Genetics, Jan. 30, 2014, vol. 10, No. 1, pp. e1004126 1-9.

* cited by examiner

*Primary Examiner* — David C Thomas
(74) *Attorney, Agent, or Firm* — Norton Rose Fulbright US LLP

(57) ABSTRACT

Embodiments of the disclosure encompass methods of amplifying nucleic acid from one or more cells. In particular embodiments, the nucleic acid is amplified as amplicons in a linear manner. Specific embodiments include the removal or effective destruction of nonlinearly produced amplicons.

13 Claims, 11 Drawing Sheets

Specification includes a Sequence Listing.

METHODS OF LINEARLY AMPLIFYING WHOLE GENOME OF A SINGLE CELL

This application is a continuation of U.S. Non-Provisional patent application Ser. No. 15/308,592 filed Nov. 2, 2016, which is a national phase application under 35 U.S.C. § 371 that claims priority to International Application No. PCT/US2015/029311 filed May 5, 2015, which claims priority to U.S. Provisional Patent Application Ser. No. 61/989,002 filed May 6, 2014, all of which are incorporated herein by reference in their entirety.

STATEMENT REGARDING FEDERALLY SPONSORED RESEARCH OR DEVELOPMENT

This invention was made with government support under EB020399 awarded by the National Institutes of Health. The government has certain rights in the invention.

TECHNICAL FIELD

Embodiments of the disclosure include the fields of nucleic acid amplification, nucleic acid manipulation, genetics, medicine, and so forth. The field of embodiments of the disclosure concerns genome or transcriptome amplification, including from one or more cells, for example.

BACKGROUND OF THE INVENTION

Great interest in single cell heterogeneity has led to recent endeavors toward single cell genome sequencing with whole-genome amplification and robustness (Navin et al., 2011; Fan et al., 2011; Lao et al., 2008; Hou et al., 2012; Cheng et al., 2011; Telenius et al., 1992; Zhang et al., 2006; Zhang et al., 1992). However, the methods used to date are generally hampered by relatively low coverage. Polymerase chain reaction (PCR) has been a gold standard for DNA amplification of specific regions. Relying on exponential amplification with random primers, PCR-based whole-genome amplification methods introduce strong sequence dependent bias, and hence are not ideal for uniform representation of the whole genome. Multiple Displacement Amplification (MDA) has been developed to overcome these shortcomings of PCR (Dean et al., 2002; Dean et al., 2001), but MDA still exhibits considerable bias. For these reasons, whole-genome sequencing of single human cells, which allows the accurate detection of single nucleotide variants (SNVs), has not been convincingly reported.

To achieve whole-genome SNV calling for a single cell with the accuracy that is comparable to the bulk sequencing, the main technological barrier is the amplification errors produced and propagated in nonlinear amplification in the current state of the art. In nonlinear amplification, the errors made by the polymerase will be copied when the newly synthesized product is used as a template in the following cycles. For regular PCR amplification where there are thousands or more templates to begin with, these errors will not cause any problem because each random error in a particular copy is diluted by the large number of other independent copies. However, for single cell amplification the scenario is different, as one only has a single copy of each unique chromosome as the template. In nonlinear amplification, the errors made in the first cycle will be possessed by half of DNA products and these errors will continue to be copied at similar percentage. Eventually in the sequencing data, these errors cannot be discriminated from true heterozygous variants in the single cell. More importantly, this false positive rate cannot be reduced simply by increasing sequencing depth. To overcome this technical problem, linear amplification is needed. When the amplification is linear, all the DNA products are copied directly from the original template. As a result, the amplification errors are independently generated and can be diluted among the linearly amplified products.

BRIEF SUMMARY OF THE INVENTION

The present invention is directed to systems, methods, and compositions for amplification of a plurality of nucleic acids. In particular embodiments, the plurality of nucleic acids is a full or partial genome of one or more cells or cell-free materials or a transcriptome of one or more cells, or cell-free materials, for example, or epigenome, i.e., the scarce nucleic acid material of the genome after bisulfide conversion, or selected genome, i.e., the scarce nucleic acid material of the genome after chromatin precipitation. The genome or transcriptome may come from a single cell or multiple cells, such as two cells, three cells, four cells, five cells, and so forth. In embodiments wherein the genome or transcriptome or epi-genome or targeted region of the genome comes from multiple cells, the multiple cells may be of the same type, genotype, or phenotype. In cases wherein the nucleic acids are derived from multiple cells, the cells may be from the same source or from the same tissue, for example. In certain embodiments, the cell is a fetal cell, cancerous cell, a cell that is suspected to be cancerous, and so forth. Cell-free nucleic acid materials include nucleic acid exist in blood or other body fluid.

Embodiments of the present disclosure relate in general to methods and compositions for amplifying genomic sequences, such as the whole genome of a single cell, or optionally multiple cells. Embodiments of the disclosure also relate in general to methods and compositions for amplifying part or all of a transcriptome, such as the entire transcriptome of a single cell, or optionally multiple cells. The skilled artisan will recognize that methods of the disclosure allow linear amplification of particular nucleic acids from a genome or transcriptome, where the resultant product of the method is a plurality of amplicons (representing part or all of the respective genome or transcriptome), and that at least in some cases the linearly produced amplicons are then further amplified in either a linear or nonlinear manner (such as by PCR).

Embodiments of the disclosure include methods for performing whole genome amplification for single cells (or optionally multiple cells) with high uniformity and high fidelity across the genome. Such methods allow accurate detection of copy number variations (CNVs) and single nucleotide variations (SNVs), for example, and optionally the presence of the CNVs or SNVs, for example, are detected by standard high throughput sequencing platforms or microarray or PCR-based genotyping following the methods of the invention.

Embodiments of methods of the disclosure provide a significant improvement of presently used methods in the art. For example, the SNV detection accuracy by linear amplification from original single cell DNA fragments covering the whole genome, i.e. creating independent copies of amplicons from single cell DNA templates, is greatly improved over methods in the art. Linear amplification allows the efficient filtering of amplification errors, therefore achieving the accuracy comparable to bulk sequencing for SNP detection, for example. Specific embodiments of methods provided herein introduce a "barcode" for each independently copied amplicon. This barcode allows the determination of the false positive rate at each loci across the genome.

Methods are provided herein that can be used to perform the amplification of DNA fragments extracted from one single cell, although in some cases the DNA may be extracted from more than one cell. Therefore, at least certain methods allow uniform whole genome amplification for one single cell, which allow accurate detection of copy number variations (CNVs) and single nucleotide variations (SNVs) by standard high throughput sequencing platforms.

Embodiments of the disclosure allow one to utilize an exact linear amplification method, which will provide accurate SNV detection with one and only one cell. No kindred cells are required to filter out the false positives, in particular cases. Embodiments of the disclosure are an improvement over the art by allowing the use of histological clinical samples as a source of cells for the nucleic acid to be amplified.

Methods are provided herein for removing the bias in amplification by separating the different DNA fragments into millions of small volume reaction compartments and conducting the amplification without the interference and competition between different amplicons. Thus, in particular embodiments a single amplicon is present in a reaction well for amplification, such as by PCR. In certain aspects, the volume of the reaction in the reaction compartment is femtoliter to nanoliter volumes.

Embodiments of methods provided herein significantly improve the uniformity by performing the amplification of each DNA fragment in separated reaction compartments in microfluidic device or separated reaction droplets created by emulsions, for example. The individual amplification is done in the tens of millions or more reaction compartments with as small as femtoliter volume, in some cases. In specific aspects, the amplification is saturated in each of the individual reactions and the nonlinear amplification (sequencing dependent PCR bias or the amplification bias of MDA) is minimized.

In specific embodiments, the methods employ polymerases that have both strong displacement strength and high association constant with a primer-DNA complex.

In one embodiment, there is a method of linearly producing amplicons from one or more cells, comprising the steps of: exposing nucleic acid from the one or more cells to a first plurality of primers and to a polymerase that comprises strand displacement activity, said exposing under conditions of a temperature range of 0° C. to about 35° C., wherein the primers anneal to the nucleic acid and the primers are extended by the polymerase, wherein the primers in the first plurality have the following characteristics: a) 40%-60% G-rich or 40%-60% C-rich; and b) comprise a restriction endonuclease site, thereby producing a mixture comprising primer-annealed nucleic acid templates; exposing the primer-annealed nucleic acid templates to two or more of extension, melting, and annealing steps, thereby producing a mixture of nucleic acid template, linearly produced semi-amplicons, and nonlinearly produced full amplicons; exposing the mixture to conditions such that the two ends of a full amplicon are capable of annealing to each other, thereby producing looped full amplicons; exposing the looped full amplicons to the restriction endonuclease, thereby rendering the full amplicons unable to be annealed to by the first plurality of primers or a second plurality of primers, wherein the second plurality of primers is 40%-60% G-rich or C-rich; and annealing and extension of the first plurality of primers or a second plurality of primers to the linearly produced semi-amplicons remaining in the mixture, wherein said annealing and extension occurs with no further melting of the nucleic acids, thereby producing linearly produced full amplicons. In a specific embodiment, the method further comprises the step of subjecting the linearly produced full amplicons to amplification. In one embodiment, a polymerase used in methods of the disclosure lacks exonuclease activity. In specific embodiments, the exposing the mixture step occurs at a temperature less than 60° C. In some cases, the method provides for further comprising obtaining the nucleic acid from the one or more cells, such as by lysis of the cell or cells and extraction of the nucleic acid therefrom. In specific embodiments, the nucleic acid comprises genomic DNA. In some cases, the nucleic acid comprises RNA and the method further comprises the step of producing cDNA from the RNA.

In embodiments of the disclosure, certain primers may be utilized, including primers in a first or second plurality, at least. In specific embodiments, the primers in the first plurality, second plurality, or both comprise the following formula:

$$X_n Y_m Z_p,$$

wherein n is greater than 2 and X is 40%-60% G-rich or 40%-60% C-rich, wherein Y is any nucleotide and m is 3-8 nucleotides and wherein Z is a G when $X_n$ is G-rich or is C when $X_n$ is C-rich, wherein p is 2-4 nucleotides. In specific cases, m is 5 nucleotides; p is 3 nucleotides; n is 20-40 nucleotides; n is 25-35 nucleotides; or n is 24-28 nucleotides. In a specific embodiment, the polymerase is Bst large fragment or pyrophage 3173 polymerase. In a specific case, the extension step of the primer-annealed nucleic acid templates occurs at a temperature range of from 30° C. to 65° C. In particular embodiments, following the extension of the primer-annealed nucleic acid templates, the nucleic acid is melted at a temperature of at least 90° C. In certain cases, following the melting of the nucleic acid, the nucleic acid is cooled to a temperature below the melting temperature of the primer and a heat-inactivatable polymerase is added. In some cases, following addition of the heat-inactivatable polymerase, there is thermal cycling at a temperature between the temperature below the Tm of the PCR primer and temperature above the Tm of the PCR primer, such as at a temperature of 58° C.-67° C. The thermal cycling may comprise 10-30 cycles, in some cases. In particular embodiments, the polymerase is heat inactivated, followed by addition of the restriction endonuclease.

In some embodiments, the primer-annealed nucleic acid templates to three to ten successive extension, melting, and annealing steps. In certain aspects, the restriction endonuclease is able to digest nucleic acid at temperatures over 50° C., such as BtsCI/BseGI. In certain embodiments, the amplification of the linearly produced full amplicons is by polymerase chain reaction (PCR) or loop mediated isothermal amplification (LAMP). In particular embodiments, at least the majority of the linearly produced full amplicons are separated from each other. In particular aspects, at least the majority of the linearly produced full amplicons are each placed in separate containers, such as wells in a microwell substrate. In certain embodiments, the wells comprise one or more amplification reaction reagents.

In particular embodiments, separately contained amplicons are subjected to amplification, such as PCR or LAMP. In some embodiments, the linearly produced full amplicons are subjected to a mixture of uracil-DNA-glycosylase and DNA glycosylase-lyase endonuclease VIII, followed by being subjected to S1 nuclease or T4 polymerase. In specific embodiments, the linearly produced full amplicons are subjected to sequencing or library construction methods. In particular embodiments, one or more of the linearly produced full amplicons is assayed for a specific nucleotide or nucleotide sequence, such as a mutation in the amplicon that is representative of a mutation in the nucleic acid. In specific embodiments, the mutation is a disease-associated mutation. In specific embodiments, the one or more cells is from a fetus, an infant, a child, or an adult. The one or more cells may be fixed in a histological preparation. In some cases, though, the one or more cells are fresh. The one or more cells may be obtained from an individual that has a medical condition or is suspected of having a medical condition, such as a genetic disease. In specific cases, the medical condition comprises cancer.

In one embodiment, there is a method of assaying nucleic acid from an individual for identifying a medical condition in the individual or identifying a risk of the individual for having the medical condition, comprising the step of comparing part or all of a sequence of linearly produced full amplicons generated by methods of the disclosure from a sample from the individual to a standard. In specific embodiments, the nucleic acid comprise genomic DNA. In some cases, the nucleic acid comprises cDNA produced from RNA from the sample. The standard may comprise nucleic acid from normal cells from the individual, such as nucleic acid from normal cells from one or more other individuals. In particular embodiments, the level of expression of nucleic acids in cells in the sample from the individual is represented in the number of linearly produced full amplicons. In some cases, the comparing step comprises comparing the number of at least some of the linearly produced full amplicons from cells in the sample from the individual to a standard. In specific embodiments, the at least some of the linearly produced full amplicons comprise one or more particular genes. In certain embodiments, the comparing step comprises assaying for the presence or absence of one or more particular nucleotides in the linearly produced full amplicons compared to the standard.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

I. Definitions

Figure 1:
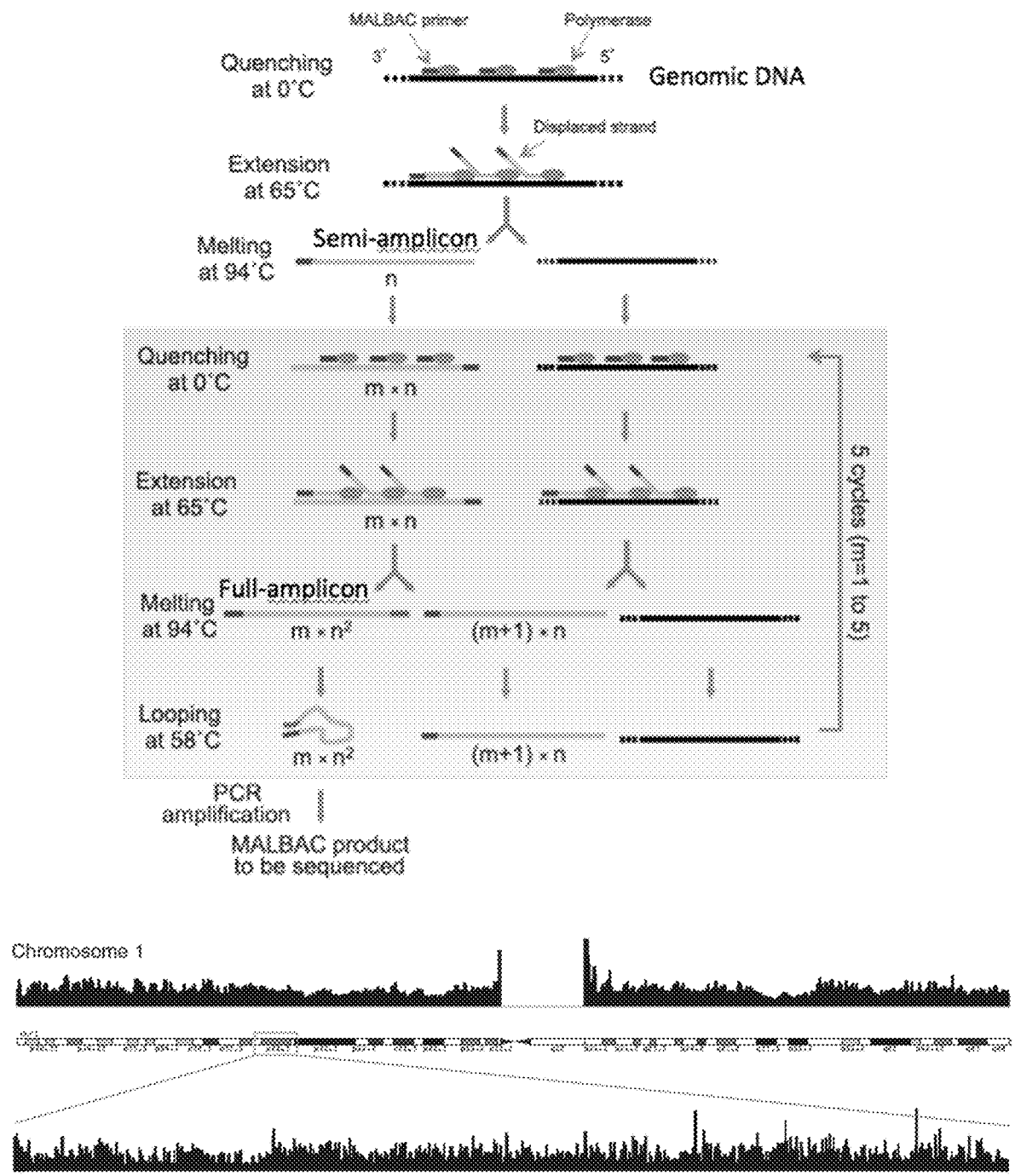
FIG. 1 illustrates an overview of a known version of amplification, referred to as Multiple Annealing and Looping Based Amplification Cycles (MALBAC). Low bias single cell whole-genome amplification (WGA). (Left) MALBAC workflow. Lysis of a single cell is followed by melting genomic DNA into single-stranded DNA molecules. MALBAC preamplification is performed prior to additional PCR amplification. First, MALBAC primers anneal randomly to single-stranded DNA molecules and are extended by a polymerase with displacement activity, which creates semi-amplicons. In the next cycle, single stranded amplicons with complementary sequences on both ends are generated. The 3' ends are protected by loop formation at intermediate temperature, which prevents the formation of chimeras and further amplification. The above cycles are repeated 5 times to generate amplicons with overlapping genome coverage that contain universal complementary sequences on both ends for subsequent PCR amplification.

As used herein, the term "semi-amplicon" refers to a polynucleotide generated by extension with a primer sequence on only one end. It is a half product of a full-amplicon.

As used herein, the term "amplicon" refers to polynucleotides that are used as templates in PCR reactions.

As used herein, the term "full-amplicon" refers to polynucleotides with primer sequences (different or complementary with each other) on two ends, readily for PCR amplification.

As used herein, the term "linear amplification" denotes that the products of amplification are directly copied from original templates, so the increase of DNA products is linear. In contrast, for nonlinear amplifications, the products are copied from both original templates and the copied products. PCR reaction, for example, is a typical nonlinear amplification with exponential increase of products. In specific aspects, linear amplification of a specific template is defined as when every (or the majority of) copies of the specific template in a plurality of copies of the template is directly produced from the specific template. In non-linear amplification of a specific template, copies of the template may be produced from another copy of the specific template.

II. General Embodiments

Embodiments of the disclosure provide amplification methods useful for amplifying part or all of nucleic acids from one or more cells. In particular aspects, the nucleic acids are part or all of the genome of the cell(s) or part or all of mRNA of the cell(s), as represented by cDNA reverse transcribed from the mRNA. The amplification methods generate linearly produced semi-amplicons and nonlinearly produced full amplicons, following which the nonlinearly produced full amplicons are literally converted to double stranded DNA with biotinylated PCR primer and to extracted from reaction by streptavidin magnetic beads or effectively removed from participation in the subsequent method steps (such as by rendering them unable to be annealed to by a particular set of primers), following which the linearly produced semi-amplicons are subjected to annealing and extension steps in the absence of a melting step to produce linearly produced full amplicons. The linearly produced full amplicons are then optionally melted and subjected to other methods, such as linear or nonlinear amplification, for example by PCR.

According to certain aspects of the disclosure, DNA from a single cell or multiple cells in the reaction mixture is subjected to amplification by at least one DNA polymerase.

According to one aspect, single cell nucleic acid amplification or multiple cell nucleic acid amplification is preceded by denaturing the double-stranded DNA from a sample to a single-stranded condition, which allows primers to anneal to the DNA. Next, the reaction temperature is lowered to a temperature that allows random nucleotides at the 3' end of the first primer to anneal to the DNA to form hybrid duplexes. After the hybrid duplexes form, one or more DNA polymerases present in the reaction mixture or provided thereto extends the complementary DNA strand from the 3' end of the first primer during an incubation period. A DNA polymerase may or may not comprise 5' to 3' exonuclease activity or strand displacement activity.

FIG. 1 shows an overview of a prior art method termed MALBAC of which the present invention is an improvement. Lysis of a single cell is followed by melting genomic DNA into single-stranded DNA molecules. MALBAC preamplification is performed prior to additional PCR amplification. First, MALBAC primers anneal randomly to single-stranded DNA molecules and are extended by a polymerase with displacement activity, which creates semi-amplicons. In the next cycle, single stranded amplicons with complementary sequences on both ends are generated. The 3' ends are protected by loop formation at intermediate temperature, which prevents the formation of chimeras and further amplification. The above cycles are repeated about 5 times (for example) to generate amplicons with overlapping genome coverage that contain universal complementary sequences on both ends for subsequent PCR amplification.

MALBAC preamplification in the art is not totally linear. In MALBAC preamplification, the semi-amplicons are copied directly from the original DNA template, so they are linearly produced. However, the semi-amplicons are used as templates in the following amplification cycles. For example, the semi-amplicon produced in the first cycle are used in the following five cycles; the semi-amplicon produced in the second cycle are used in the following four cycles, etc. During the amplification, if the polymerase makes an error in a semi-amplicon in the first cycle, the error will be copied for five times in the following amplification cycles. By constituting 30% of final reads, this amplification error could be taken as a mutation. As a result, one would need to sequence at least three kindred cells for accurate single nucleotide variant (SNV) calling, for example.

Figure 2:
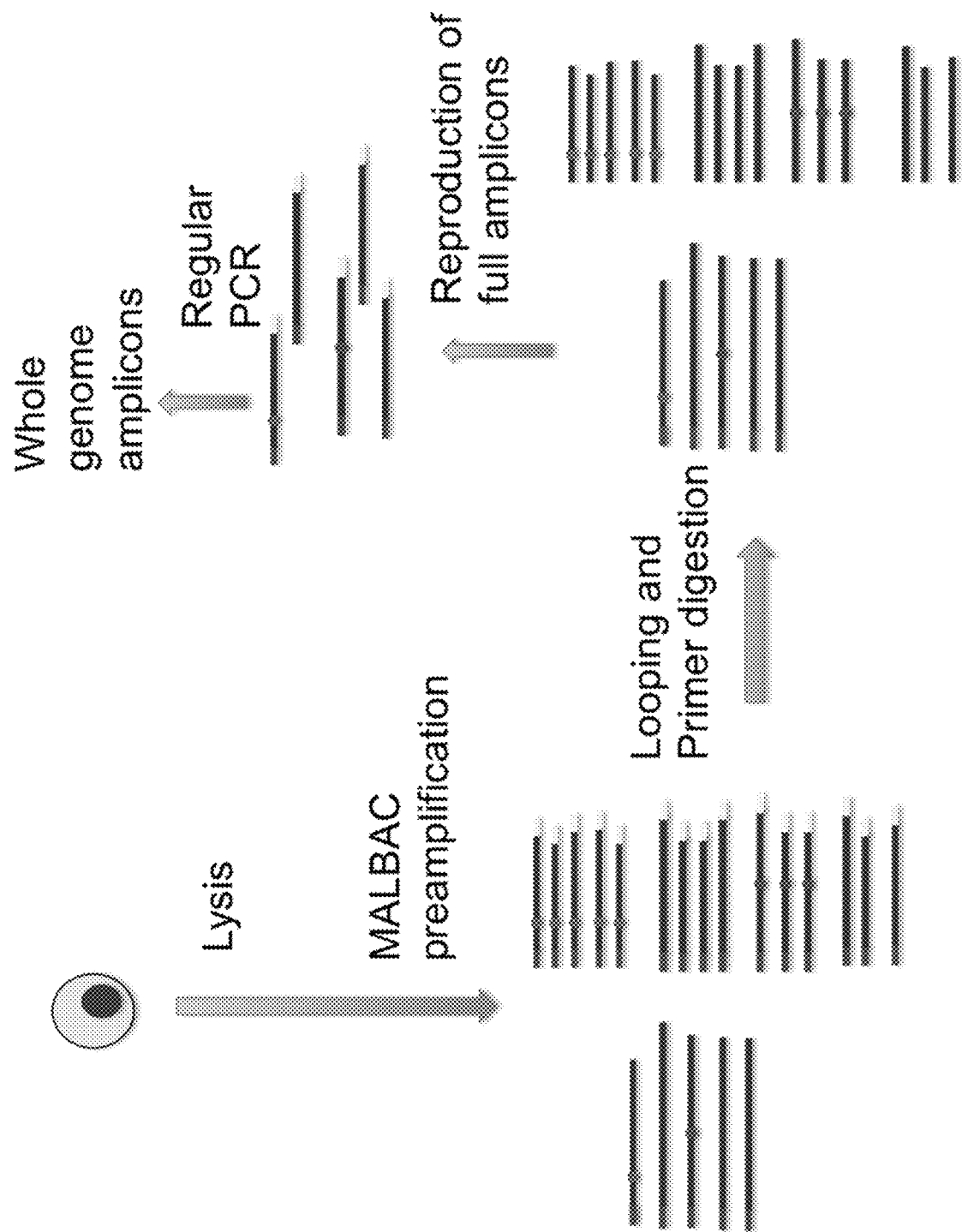
FIG. 2 provides an overview of an embodiment of the inventive amplification scheme. In this scheme, one does not use the full amplicons produced in MALBAC for PCR amplification. Instead, one removes the primer sequence of the looped full amplicons, such as by digestion. After that, one can reproduce the full amplicons linearly for the semi-amplicons, which are linearly produced from the original genomic template. This entirely linear amplified full amplicons are used in the following PCR amplification, for example.

To overcome this technical variability, embodiments of the disclosure provide a new procedure to achieve true linear pre-amplification. Because the semi-amplicons are linearly produced, it is useful to have these semi-amplicons linearly copied to the full amplicons without any distortion. Such an achievement would provide an amplification scheme that is entirely linear. To achieve that, embodiments of the disclosure encompass what is shown in FIG. 2; after the pre-amplification, instead of then employing downstream PCR amplification (for example), one can use an appropriate restriction enzyme to cut the primer sequence region in the looped full amplicons. The full amplicons can also be converted to double stranded DNA with biotinylated PCR primer and then extracted from reaction by streptavidin magnetic beads. Meanwhile, single-stranded semi-amplicons remain intact. In the following step, one can deactivate the restriction enzyme and recreate new full amplicons from the semi-amplicons all at once to guarantee linear representation (FIG. 2).). The full amplicons can be reproduced by one or more rounds and annealing and extension steps. Alternatively the semi-amplicons can be tailed and the tailed region can be hybridized with a new primer to generate the full amplicons.

Thus, embodiments of the invention include methods of linearly amplifying nucleic acid from one or more cells. The method in some aspects begins with a provided nucleic acid sample, although in some cases the nucleic acid must be obtained from the cell(s), such as by routine methods. When amplifying DNA, the totality of nucleic acid extracted from the cell(s) may be subjected to RNAase. When amplifying the transcriptome (in the form of cDNA from the mRNA), the totality of nucleic acid may be subjected to DNAase prior to reverse transcription of the mRNA. Nucleic acid from one or more cells is exposed to a first plurality of primers and the cells are also exposed to a polymerase that comprises strand displacement activity; such a step occurs under conditions of a temperature range of 0° C. to about 30° C., for example. In such a step, the primers anneal to the nucleic acid and the primers are extended by the polymerase. In specific embodiments, the primers in the first plurality are 40%-60% G-rich or 40%-60% C-rich and also comprise a restriction endonuclease site. Upon exposure of the primers to the nucleic acid, this generates a mixture comprising primer-annealed nucleic acid templates. The primer-annealed nucleic acid templates are then allowed to be subjected to two or more extension, melting, and annealing steps, and such steps produce a mixture of nucleic acid template, linearly produced semi-amplicons, and nonlinearly produced full amplicons. The mixture then is exposed to conditions such that the two ends of a full amplicon are capable of annealing to each other, which thereby results in looped full amplicons. The looped full amplicons are then exposed to a restriction endonuclease that is capable of digesting the annealed ends of the looped full amplicon. Upon doing so, the full amplicons are no longer able to be annealed to by at least certain primers, including the first plurality of primers or a second plurality of primers, wherein the second plurality of primers is 40%-60% G-rich or C-rich. The linearly produced semi-amplicons remaining in the mixture may be annealed to by the first plurality of primers or a second plurality of primers and extended. The annealing and extension occurs with no further melting of the nucleic acids, thereby producing linearly produced full amplicons. In some cases, the linearly produced full amplicons are further amplified, such as by nonlinear or linear methods, including standard PCR methods, for example.

In embodiments of the invention, one can achieve the first exact linear amplification method for single cell whole genome (or transciptome) amplification. With the sensitivity and accuracy allowed by this innovation for single cell SNV (for example) detection, methods and compositions of the disclosure can generate a broad impact in biological and/or clinical research and use.

In embodiments of the disclosure, methods are provided that can efficiently remove preexisting primers to allow efficient tailing of semiamplicons. Without inefficient digestion of primers, the tailing of residual primers out competes the tailing of semiamplicons and leads to the failure of amplification in the following step. Thus, in specific embodiments, there is provided efficient digestion of preexisting primers, therefore the successful generation and amplification of full amplicons is achieved.

One can use T4 polymerase or other polymerases with exonuclease activities at low temperature below (30° C. or below) and ExoI exnuclease or other exnucleases that only digest single stranded DNA. The enzymes can be heat inactivated. Tailing studies can be conducted with high concentrated C base. The dC tailed region may be hybridized with GAT5N3G primer only for producing the full amplicons, in specific embodiments.

III. Barcodes

Figure 3:
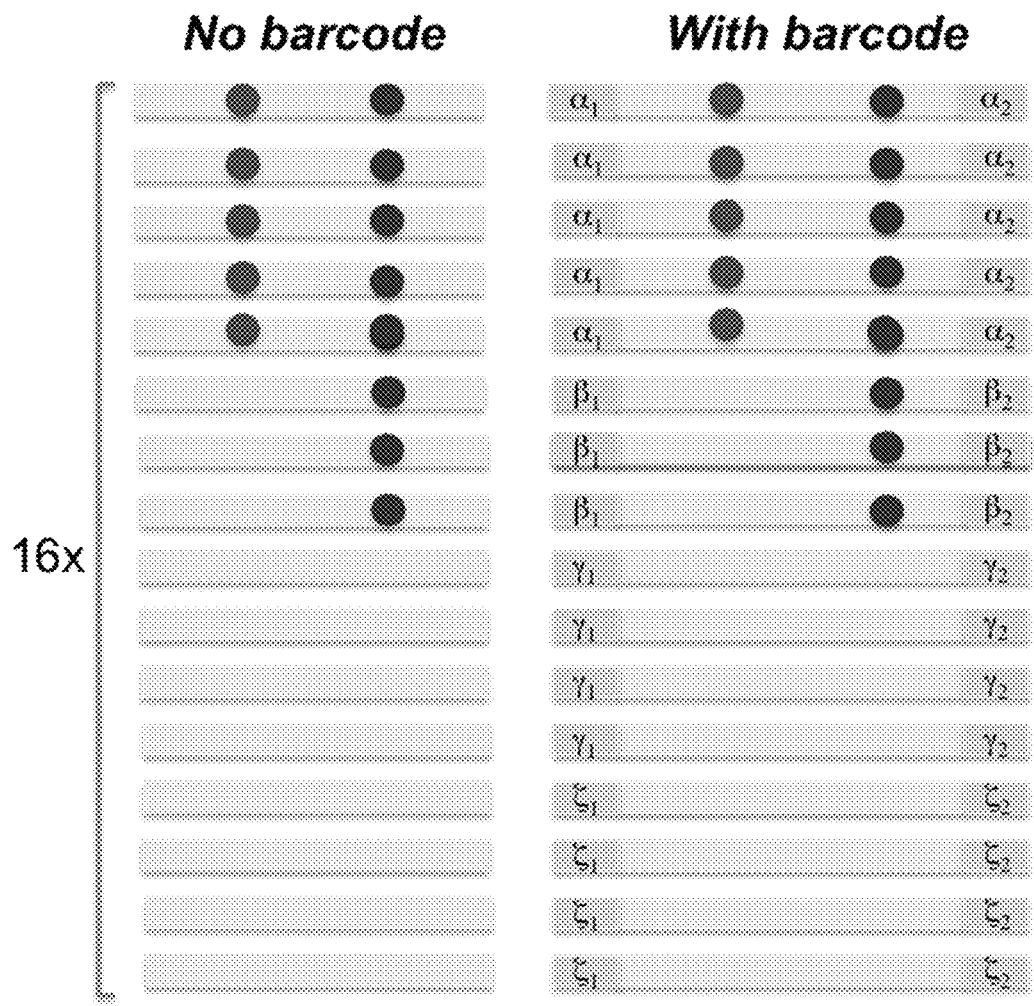
FIG. 3 shows an overview of barcode sequencing. The sequencing reads are aligned. There are two potential heterozygous mutations represented by red and blue dots (in black and white, these are respectively the left and right dots in each column). In the left panel, the sequencing reads do not possess the barcode, as the result, both mutations are called. As comparison, the sequencing reads in the right panel possess the barcodes: α, β, γ and ζ, which represent independent DNA copies generated in linear amplification. It is evident that the mutation labeled by the red dot is clearly a false positive (represented by reads with only one barcode) comparing to the mutation labeled by the blue dot (represented by reads with two different barcodes)

Although the scheme of FIG. 2 is schematically linear, in some embodiments one could address situations in which not all of the semi-amplicons are efficiently copied to the full amplicons, for example in the last cycles. As a result of this aspect, at least in some cases one may have a limited number of independent full-amplicons. If this number was less than four copies (for example), one would still have difficulties to discriminate the true mutations from the amplification errors. In particular aspects, one needs to have enough number of independent copies of the original template in order to dilute the amplification errors in the final read presentation. To address this issue, one can also introduce random "barcodes" (random DNA sequence with variable length (for example NNNNN, where N represents mixture of four nucleotides) into the primers, which will index each linearly amplified semiamplicon and register each full amplicon to the corresponding semi-amplicon (FIG. 3). By indexing each of the read with barcodes, one can evaluate whether the reads are linearly distributed. In the case of residual nonlinearity, one can use the barcode to identify amplification errors and improve the accuracy of SNV calling, as shown in FIG. 3.

IV. Exemplary Applications of Methods of the Disclosure

Methods of the disclosure may be utilized in research, clinical, and/or other applications. In particular embodiments, methods of the disclosure are utilized in diagnostics and/or prognostics and/or monitoring of one or more therapies for an individual, metagenomic analysis for microbes and forensic DNA test, for example.

In one example of an application of one or more methods of the disclosure, the method is utilized for assaying for one or more variations in content or expression level of a nucleic acid from an individual; the variation may be in relation to a known standard, for example, such as a corresponding wild-type sequence of a particular nucleic acid. The variation in content may comprise one or more nucleotide differences compared to wild-type, such as a substitution, deletion, inversion, and so forth. The variation in expression may comprise upregulation or downregulation compared to normal expression levels of a particular known or determined standard. The standard may comprise the content of normal nucleic acid content or expression level in cells known to be normal in genotype and/or phenotype.

In specific cases, the nucleic acid being assayed for is obtained from a sample from an individual that has a medical condition or is suspected of having a medical condition or is at risk for having a medical condition or is undergoing therapy for a medical condition. The sample may be of any kind so long as nucleic acid may be obtained directly or indirectly from one or more cells from the sample. In particular embodiments, the nucleic acid is obtained from one or more cells from a sample from the individual. The sample may be blood, tissue, hair, biopsy, urine, nipple aspirate, amniotic fluid, cheek scrapings, fecal matter, or embryos.

An appropriate sample from the individual is obtained, and the methods of the disclosure may be performed directly or indirectly by the individual that obtained the sample or the methods may be performed by another party or parties.

A. Genetic Testing

In particular applications, one or more particular nucleic acid sequences are desired to be known in a sample from an individual. The individual may be of any age. The individual may be subjected to routine testing or may have a particular desire or medical reason for being tested. The individual may be suspected of having a particular medical condition, such as from having one or more symptoms associated with the medical condition and/or having a personal or family history associated with the medical condition. The individual may be at risk for having a medical condition, such as having a family history with the medical condition or having one or more known risk factors for the medical condition, such as high cholesterol for heart disease, being a smoker for a variety of medical conditions, having high blood pressure for heart disease or stroke, having a genetic marker associated with the medical condition, and so forth.

In specific cases, the individual is a fetus and the fetus may or may not be suspected of having a particular nucleic acid sequence or nucleic acid expression variance compared to wild type, such sequence content or expression variance associated with a medical condition. In some cases, the fetus is at risk for a particular medical condition because of family history or environmental risk (i.e., radiation) or high-age pregnancy, for example, although the fetus may be needed to be tested for routine purposes. In such cases wherein a particular sequence(s) content or expression level is desired to be known from a fetus, a sample is taken that comprises one or more fetal cells. The sample may be a biopsy from the fetus, although in particular cases the sample is amniotic fluid or maternal blood or embryos at early stage of development.

In one aspect of the disclosure, amniotic fluid from a pregnant mother is obtained and one or more fetal cells are isolated therefrom. The fetal cell isolation may occur by routine methods in the art, such as by utilizing a marker on the surface of the fetal cell to distinguishes the fetal cell(s) from the maternal cell(s). Three different types of fetal cells could exist in maternal circulation: trophoblasts, leukocytes and fetal erythrocytes (nucleated red blood cells). The most promising cell for enrichment is fetal erythrocytes, which can be identified by size column selection, followed by CD71-antibody staining or epsilon-globin chain immunophenotyping and then scanning or sorting based on fluorescence intensity, in certain embodiments.

Once the fetal cell(s) is isolated, nucleic acids are extracted therefrom, such as by routine methods in the art. The nucleic acid from the fetal cell(s) is subjected to methods of the disclosure to produce linearly generated amplicons that cover at least part, most, or all of the genome of the fetal cell(s). Following linear amplification, one or more sequences of the amplicons may be further amplified and also may be sequenced, at least in part, or may be subjected to microarray techniques. In specific embodiments, a SNV or CNV is assayed for, and the results of the assay are utilized in determination of whether or not the corresponding fetus has a particular medical condition or is susceptible to having a particular medical condition, for example. In specific cases, the fetus may be treated for the medical condition or may be subjected to methods of prevention or delay of onset of the medical condition, and this may occur in utero and/or following birth, for example.

Although the fetal sample may be assayed for the presence of a SNV or CNV (either of which may be disease-associated or disease-causing), in particular embodiments the fetal sample is assayed for a genetic mutation associated with any particular medical condition. Examples of genes associated with prenatal medical conditions that may be assayed for include one or more of the following: ACAD8, ACADSB, ACSF3, C7orf10, IFITM5, MTR, CYP11B1, CYP17A1, GNMT, HPD, TAT, AHCY, AGA, PLOD2, ATP5A1, C12orf65, MARS2, MRPL40, MTFMT, SERPINF1, FARS2, ALPL, TYROBP, GFM1, ACAT1, TFB1M, MRRF, MRPS2, MRPS22, MRPL44, MRPS18A, NARS2, HARS2, SARS2, AARS2, KARS, PLODS, FBN1, FKBP10, RPGRIP1, RPGR, DFNB31, GPR98, PCDH15, USH1C, CERKL, CDHR1, LCA5, PROM1, TTC8, MFRP, ABHD12 CEP290, C8orf37, LEMD3, AIPL1, GUCY2D, CTSK, RP2, IMPG2, PDE6B, RBP3, PRCD, RLBP1, RGR, SAG, FLVCR1, ZNF513, MAK, NDUFB6, TMLHE, ALDOA, PGM1, ENO3, LARS2, ATP7A, ATP7B, TNFRSF11B, LMBRD1, MTRR, FAM123B, FAM20C, ANKH, TGFB1, SOST, TNFRSF11A, CA2, OSTM1, CLCN7, PPIB, TCIRG1, SLC39A13. COL1A2, TNFSF11, SLC34A1, NDUFAF5, FOXRED1, NDUFA2, NDUFA8, NDUFA10, NDUFA11, NDUFA13, NDUFAF3, SP7, NDUFS1, NDUFV3, NUBPL, TTC19, UQCRB, UQCRQ, COX4I1, COX4I2, COX7A1, TACO1, COL3A1, SLC9A3R1, CA4, FSCN2, BCKDHA, GUCA1B, KLHL7, IMPDH1, PRPF6, PRPF31, PRPF8, PRPF3, ROM1, SNRNP200, RP9, APRT, RD3, LRAT, TULP1, CRB1, SPATA7, USH1G, ACACB, BCKDHB, ACACA, TOPORS, PRKCG, NRL, NR2E3, RP1, RHO, BEST1, SEMA4A, RPE65, PRPH2, CNGB1, CNGA1, CRX, RDH12, C2orf71, DHDDS, EYS, IDH3B, MERTK, PDE6A, FAM161A, PDE6G, TYMP (ECGF1), POLG (POLG1, POLGA), TK2, DGUOK (dGK), SURF1, SCO2 (SCOW, SCO1, COX10, BCS1L, ACADM, HADHA, ALDOB, G6PC (GSD1a), PAH (PH), OTC, GAMT, SLC6A8, SLC25A13, CPT2, PDHA1, SLC25A4 (ANTI), C10orf2 (TWINKLE), SDHA, SLC25A15, LRPPRC, GALT, PMM2, ATPAF2 (ATP12), GALE, LPIN1, ATP5E, B4GALT7, ATP8B1 (ATPIC, PFIC), ABCB11 (ABC16, PFIC-2, PGY4), ABCB4 (GBD1, MDR2, PFIC-3), MPV17 (SYM1), TIMM8A (DDP, MTS), CPS1, NAGS, ACADVL, SLC22A5 (OCTN2), CPT1A (CPT1-L, L-CPT1), CPT1B, SUCLA2, POLG2 (HP55, MTPOLB), ACADL, SUCLG1, MCEE, GAA, PDSS1 (COQ1, TPT), PDSS2 (bA59I9.3), COQ2 (CL640, F1126072), RRM2B (p53R2), ARG1, SLC25A20 (CACT), MMACHC (cblC), FAH, MPI, GATM, OPA1, TFAM, TOMM20 (MAS20P, TOM20), NDUFAF4 (HRPAP20, C6orf66), NDUFA1 (CI-MWFE, MWFE), SLC25A3 (PHC), BTD, OPA3 (F1122187, MGA3), GYS2, NDUFAF2 (B17.2L, MMTN), HLCS (HCS), COX15, FASTKD2, NDUFS4, NDUFS6, NDUFS3, MMAA (cb1A), MUT, NDUFV1, MOCS1, NDUFS7 (PSST), TAZ (BTHS, G4.5, XAP-2), MOCS2, COX6B1 (COXG), HADHB, MCCC1 (MCCA), MCCC2 (MCCB), TSFM (EF-TS, EF-Tsmt), PUS1, ISCU, AGL, SDHAF1, IVD, GCDH, ADSL, DARS2, RARS2, TMEM70, ETHE1, PC, JAG1, MRPS16, PCCA, PCCB, COQ9, LDHA, PYGL, GALK1, PYGM, PGAM2, TUFM, TRMU, PFKM, GBE1, SLC37A4, GYS1, ETFDH, NDUFS8, CABC1 (ADCK3), ETFA, ETFB, DBT, SLC25A19, MMADHC, PDP1, PDHB, ACAD9, AUH, DLAT, PDHX, ACADS, NDUFS2, FBP1, NDUFAF1 (CIA30, CGI65), YARS2, SUCLG2, TCN2, CBS, PHKB, PHKG2, PHKA1, PHKA2, LIPA, ASL, HPRT1, OCRL, PNP, TSHR, ADA, ARSB, ALDH5A1, PNP, AMT, DECR1, HSD17B10, IYD, IL2RG, MGME1, HMGCL, IQCB1, OTX2, KCNJ13, CABP4, NMNAT1, ALG2, DOLK, ABCD4, ALDH4A1, ALG1, GPR143, UBE3A, ARX, GJB2 (CX26, NSRD1), APC, HTT, IKBKG (NEMO), DMPK, PTPN11, MECP2, MECP2, RECQL4, ATXN1, ATXN10, RMRP, CDKL5, PLP1, GLA, DMD, RUNX2, PLP1, CHD7, ASS1, AIRE, EIF2B, LDLR, HPRT1, RPS19, LMX1B, COL10A1, CRTAP, LEPRE1, PORCN, ASL, CFTR, ARSA, IDUA, IDS, MYO7A, GLANS, GALC, KRAS, SOS1, RAF1, AR, PTEN, BLM, SLC9A6, HRAS, GJC2 (GJA12), NPC1, NPC2, FMR1, FMR1, PLOD1, COL2A1, COL5A1, COL5A2, ABCA4, FOXG1, TINF2, USH2A, CDH23, CLRN1, CREBBP, ABCA4, POU3F4, NRAS, CHRNA7, FOXF1, MEF2C, DHCR7, RAIL VHL, TYR (OCAIA), OCA2 (BEY, BEY1, BEY2, EYCL), TYRP1 (b-PROTEIN, CATB, GP75, SLC45A2 (AIM-1), PCDH19, SHOC2, BRAF, MAP2K1, MAP2K2, HEXA, STXBP1, ALDH7A1, SLC2A1, WDR62, MAGEL2, SDHB, and FH.

B. Cancer Testing

In some embodiments of the disclosure, a sample from an individual that has cancer or is suspected of having cancer or is being monitored for cancer therapy outcome is subjected to methods of the disclosure. Other diagnostic or prognostic tests may be run on the sample or similar samples in addition to the methods of the disclosure. The sample may be obtained by routine methods and may include a biopsy comprising cells or tissue that appears to be, is suspected of being, or is known to be cancerous. Exemplary samples for cancer testing include blood, urine, biopsy, fecal matter, nipple aspirate, cheek scrapings and so forth. In some cases, a sample is obtained from an individual at risk for having cancer; such an individual may have a family and/or personal history, may have been exposed to environmental conditions known or suspected to cause cancer, may be known to have a genetic marker associated with at least one type of cancer, and so forth. Particular types of biopsies include of the skin, lung, breast, colon, cervix, liver, kidney, prostate, and so forth.

In particular embodiments, the sample being tested from an individual is subjected to methods of the disclosure related to assaying for variance in sequence content compared to a known sample or variance in expression level of a sequence compared to normal levels (such as upregulation or downregulation of one or more genes). In some cases, the expression level of one or more particular genes as represented in the amplicon quantities produced by methods of the disclosure is indicative of the presence of cancer or risk for having the cancer or success in therapy for the cancer.

Examples of genes that may be assayed for association with a particular cancer include APC, MLH1, MSH2, MSH6, PMS2, MUTYH (MYH), RECQL4, TP53 (LFS1, p53), PTEN, RUNX1, TPMT, VHL, EPCAM (TACSTD1), ERBB2 (HER2/neu), ALK, RET, EGFR, MET, IGH, ROS1. BRAF, NPM1, JAK2, MPL, AKT1 (AKT), PIK3CA, FLT3, IGVH, CEBPA, MAX, KIT, KRAS, NF1, SDHAF2, SDHB, SDHC, SDHD, TMEM127, BMPR1A, SMAD4, STK11, BRCA1, BRCA2, CDH1, PALB2, CDKN1C, FH, FLCN, GPC3, PALB2, WT1, CDC73, MEN1, PRKAR1A, ATM, NBN, NF2, PHOX2B, PTCH1, SUFU, and/or UGT1A1.

Sample Processing and Nucleic Acids from Cells of the Invention

One or more samples from an individual being tested with methods of the disclosure may be obtained by any appropriate means. The sample may be processed prior to steps for extracting the nucleic acid, in certain embodiments. The sample may be fresh at the time the nucleic acid is extracted, or the sample may have been subjected to fixation or other processing techniques at the time the nucleic acid is extracted.

The sample may be of any kind. In embodiments wherein a cell or cells of interest are comprised among other cells, the cell or cells of interest may be isolated based on a unique feature of the desired cell or cells, such as a protein expressed on the surface of the cell. In embodiments wherein a fetal cell is isolated based on a cell marker, the cell marker may be CD71 or epsilon-globin chain, etc. In embodiments wherein a cancer cell is isolated based on a cancer marker, the cell marker may be ER/PR, Her-2/neu, EGFR, KRAS, BRAF, PDFGR, UGT1A1, etc. (Bigbee W, Herberman R B. Tumor markers and immunodiagnosis. In: Bast RC Jr., Kufe D W, Pollock R E, et al., editors. Cancer Medicine. 6th ed. Hamilton, Ontario, Canada: BC Decker Inc., 2003.)

The isolated cell can be lysed by incubating the cell in lysis buffer with surfactant (i.e. Trion-X100, tweet-20, NP-40, etc.) with protease (i.e. protein kinase K). The cells can also be lysed by alkaline solution (i.e. the detergent sodium dodecyl sulfate ($C_{12}H_{25}SO_4Na$) and a strong base such as sodium hydroxide) and this will lead to denaturation of double stranded DNA. The basic solution is neutralized by potassium or sodium acetate.

VI. Kits of the Invention

Any of the compositions described herein or similar thereto may be comprised in a kit. In a non-limiting example, one or more reagents for use in methods for amplification of nucleic acid may be comprised in a kit. Such reagents may include enzymes, buffers, nucleotides, salts, primers, and so forth. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, or may be a substrate with multiple compartments for a desired reaction.

Some components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile acceptable buffer and/or other diluent.

In specific embodiments, reagents and materials include primers for amplifying desired sequences, nucleotides, suitable buffers or buffer reagents, salt, and so forth, and in some cases the reagents include apparatus or reagents for isolation of a particular desired cell(s).

In particular embodiments, there are one or more apparatuses in the kit suitable for extracting one or more samples from an individual. The apparatus may be a syringe, fine needles, scalpel, and so forth.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation of Complete Single Cells from Tissue Sample

Histological tissue slides are prepared using commercial cryostat. Sections were prepared of 100-200 μm thickness of paraformaldehyde-fixed solid tissue. The cells of interest are cut from the section slide by laser microdissection microscopes (Leica, MMI etc.). The individual cells are dissociated from the microdissected tissue section using standard cell dissociation protocols. The complete single cells are collected into individual tubes. The individual cells are lysed in 3 to 50 Lysis buffer (30 mM Tris-Cl PH 7.8, 2 mM EDTA, 20 mM KCl, 0.2% Triton X-100, 12 μg/ml Qiagen Protease) is added to the side of the PCR tube and span down. The captured cell is then thermally lysed using the using following temperature schedule on PCR machine: 50° C. 2 hours, 75° C. 20 minutes, 80° C. 5 minutes.

Figure 4:
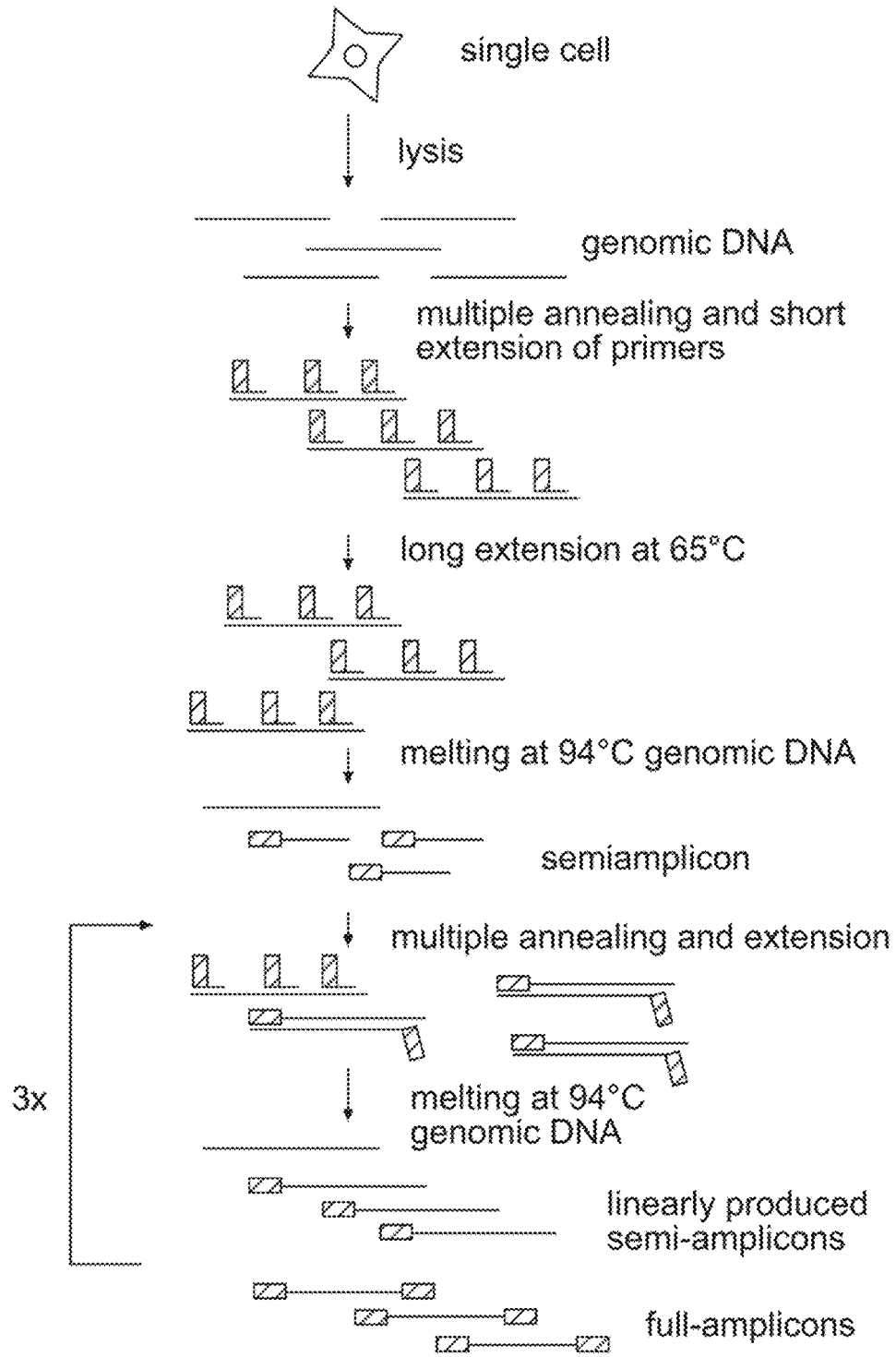
FIG. 4 shows an example of a linear production of semiamplicons.

Multiple Cycles for Linear Production of Semi-amplicons (FIG. 4)

In the first round of amplification, a pair of quasi-degenerated primers is used to initiate overlapped amplicons throughout the genomic DNA. The primers are denoted below as NG and NT primers:

```
NG primer
                                       (SEQ ID NO: 1)
5'-GTGAGTGATGGTTGAGGATGAGTGGT NNNNNGGG-3'

NT primer
                                       (SEQ ID NO: 2)
5'-GTGAGTGATGGTTGAGGATGAGTGGT NNNNNTTT-3'
```

The following buffer is included into the PCR tube and is used for the first amplification: 6.0 μl ThermoPol Buffer (NEB), 1.0 μl dNTP (10 mM), 26 μl H₂O (UV treated) and 0.3 μl NG & NT primer (100 μM).

After the PCR buffer is added into a PCR tube containing the lysed single cell, the sample is heated at 94° C. for 1-2 minutes to denature the DNA into single stranded DNA. The sample is quenched immediately into ice and is brought to a temperature of about 0° C. during which primer annealing takes place. 0.6 μl of a mixture of polymerases Bst large fragment is then added into the PCR tube. The following temperature cycles are run on the PCR machine. In the second and subsequent cycles, the PCR tube is then transferred to ice to quench the reaction and initiate new priming. A fresh mixture of the polymerases is added to the PCR tube and the following cycles are run on the PCR machine to produce amplicons.

Step 1: 10° C. —45 seconds
Step 2: 20° C. —45 seconds
Step 3: 30° C. —45 seconds
Step 4: 40° C. —30 seconds
Step 5: 55° C. —30 seconds
Repeat Step 1-5 for 4×
Step 6: 65° C. —60 seconds
Step 7: 95° C. —20 seconds
Step 8: Quench on ice and refill polymerase
Repeat Step 1-8 for N times
4° C.—∞

This times N for the repeat can be adjusted according to the condition. In certain embodiments, N is three.

Double Strand Conversion of Full Amplicons

The products from the above procedures are the mixture of full amplicons and semi-amplicons. The 0.3 μl of 100 μM PCR primer is added into the reaction and the following thermal cycling procedure (for example: 58° C. 20 seconds-70° C.—10 seconds, repeat 30 times) is performed to convert the full-amplicons into double stranded DNA, while the single stranded semi-amplicons remain the same. Following the above double stranded conversion.

```
PCR primer:
                                       (SEQ ID NO: 4)
GTGAGTGATGGTTGAGGATGAGTGGT
```

Restriction Digestion of Null Amplicons

The products from the above thermal cycles include both linearly amplified semi-amplicons and nonlinearly amplified full amplicons. The temperature is heated to 94° C. for 30 seconds to melt double strand DNA products and then kept at 50° C. At 50° C., full amplicons will form the looped since the 5' end sequence is complementary to 3' end sequencing, while semiamplicons exist as single strand DNA. Primer sequence incorporates GGATG sequence motif, which restriction enzyme BtsCI can recognize and cut the DNA. As a result, more than half primer sequence of full amplicons is deleted and therefore the digested DNA products can no longer be amplified in downstream PCR reaction. Following digestion, the temperature is raised to the range of 72° C. to 80° C. to deactivate the restriction enzymes.

Figure 5:
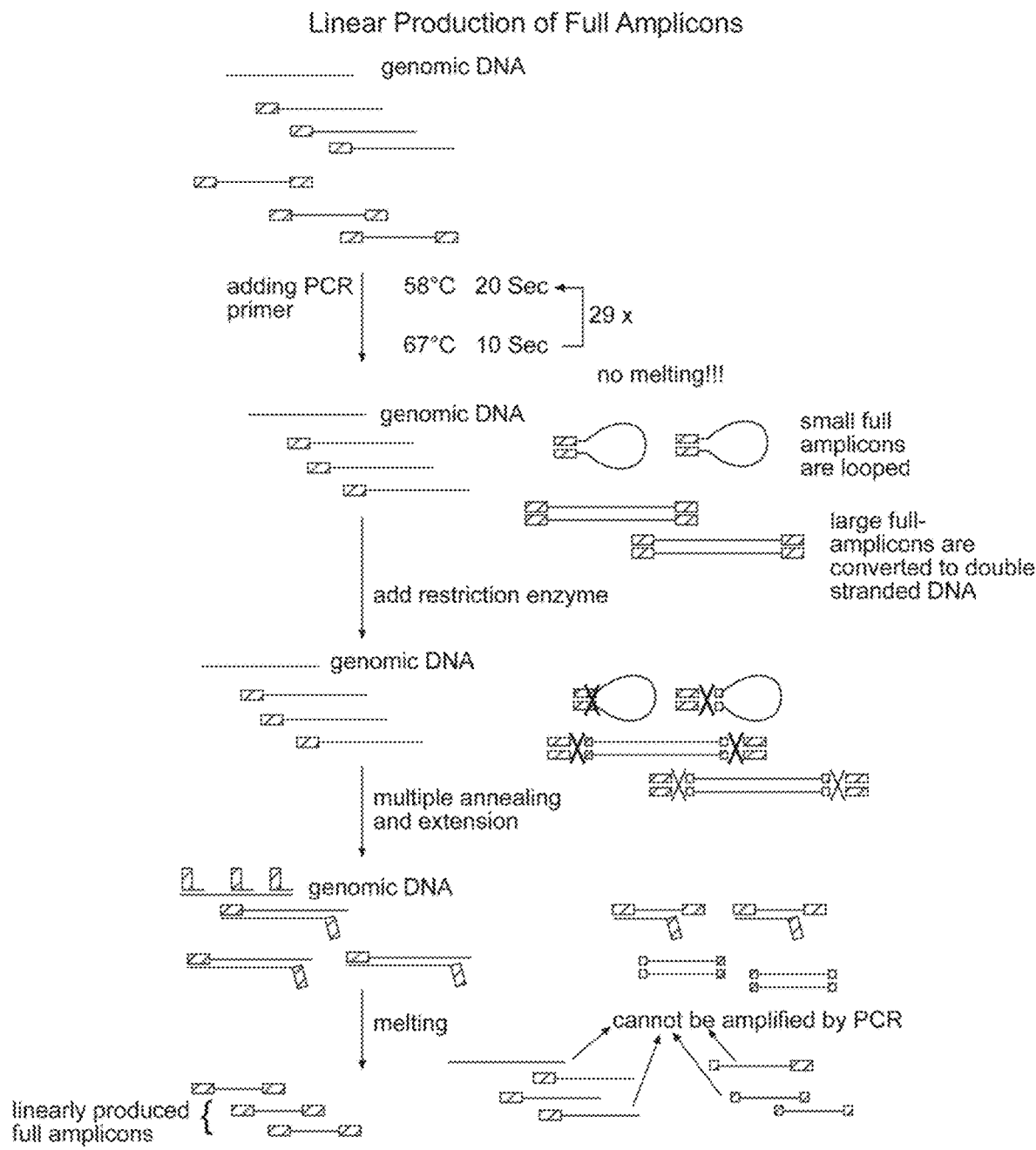
FIG. 5 illustrates an embodiment of linear production of full amplicons.

Linear Production of Full Amplicons (FIG. 5)

Figure 9:
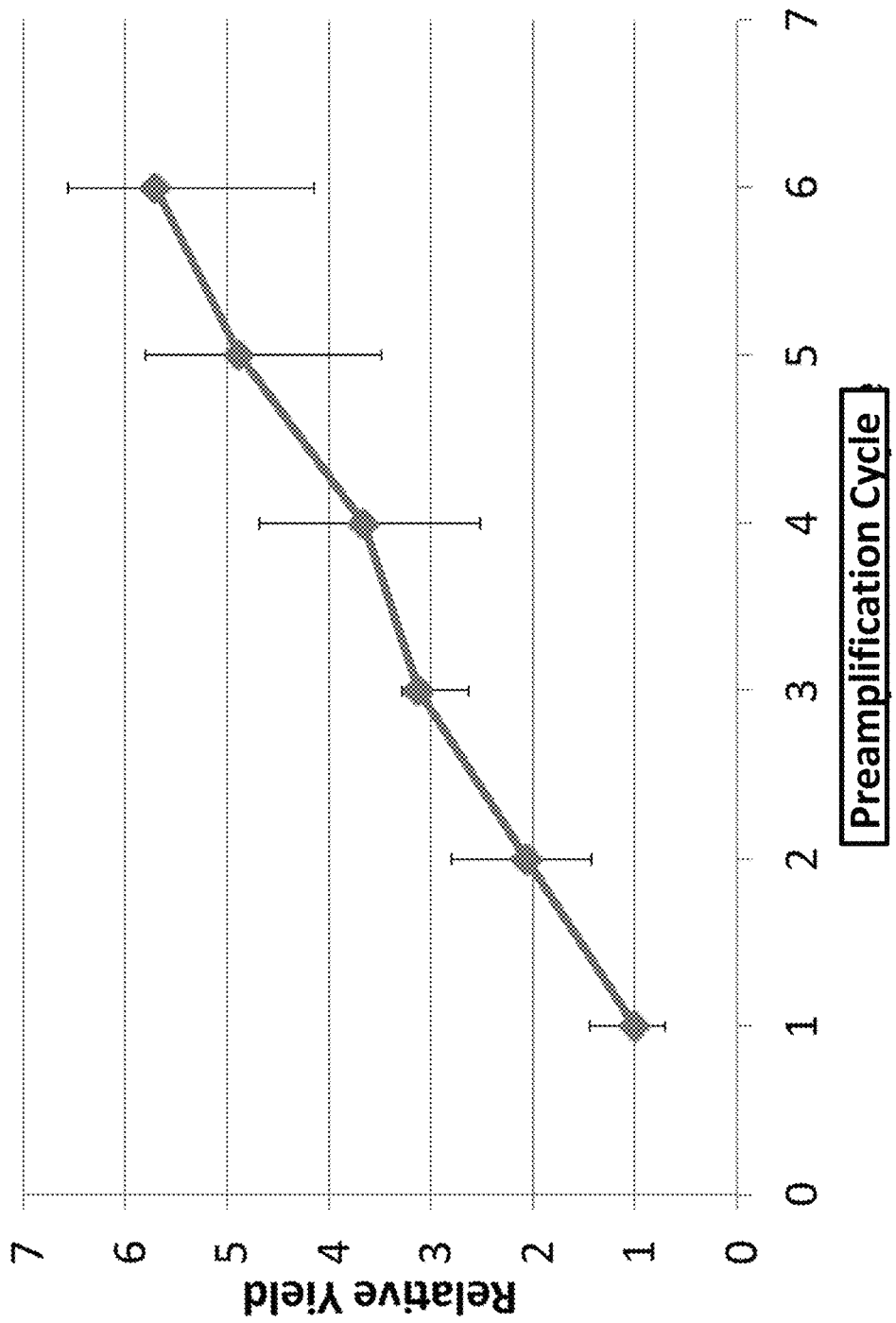
FIG. 9. The linear relation between the yield and the number of amplification cycles. This data demonstrates the success of the linear amplification. The x-axis indicates the number of preamplification cycles. The y-axis indicates the amplicon yield measured by qPCR. The linear relation confirms that the linear amplification is achieved. The experimental procedures follow the description in Example 1.

After the above digestion, the sample is heated at 94° C. for 20 seconds to denature the DNA into single stranded DNA. The sample is quenched immediately into ice and is brought to a temperature of about 0° C. during which primer annealing takes place. Following that, refill the polymerase and perform the thermal cycles below to linearly reproduce full amplicons from the amplified semiamplicons. The semi-amplicons can also be split into multiple tubes and proceed the following multiple annealing steps to create amplicons. The linear yield of amplicons is shown in FIG. 9.

Step1: 10° C.—45 seconds
Step2: 20° C.—45 seconds
Step3: 30° C.—45 seconds
Step4: 40° C.—30 seconds
Step5: 55° C.—30 seconds
Repeat Step1-5 for 4×
Step6: 65° C.—60 seconds Alternatively, the semiamplicons can also be split into multiple tubes and proceed with the following examples of digestion, tailing and extension steps to create amplicons:

The preamplification is digested by the combination of T4 polymerase and ExoI nuclease as follows: add 0.4 ul ExoI and digest at 25° C. for 30 minutes and then add 0.4 ul T4 polymerase, digest at 25° C. for 150 minutes. The enzymes are heat inactivated at 80° C. for 20 minutes before proceeding to the tailing procedure.

10×TdT reaction buffer is constituted of 0.35 ul TdT buffer, 0.4 ul 100 mM dCTP 0.4 ul, 0.1 ul TdT terminal transferase 0.1 ul and 2.75 ul H2O. Add the TdT mix into sample, mix well and use the following temperature to conduct tailing reaction: 37° C. 15 min and 72° C. 15 min.

After tailing, the following extension buffer is added (1.5 ul 10× Thermopol, 1.25 ul dNTP (10 uM each), 1.25 ul 10 uM GAT21 5n3G and 12 ul H2O). After mixing well the reaction, place the sample on the block at 95° C. for 1 min, lower the temperature 50° C. hold for at least 20 s; add deepvent DNA polymerase 0.4 ul or other polymerases, mix well and conduct the following cycles:

Step 1: 50° C. 45 s
Step 2: 72° C. 45 s
Repeat Step 1 to 2 for 10 cycles

Example 2

Single Tube or Multiple Tube Amplification of Amplicons Using Standard Methods

The following reaction buffer is prepared and added to the PCR tube which is being maintained on ice.
3.0 μl ThermoPol Buffer (NEB)
1.0 μl dNTP (10 mM)
26 μl H₂O (UV treated)

```
0.1 µl primer (100 µM)
                                          SEQ ID NO: 5)
(5'-GTGAGTGATGGTTGAGGATGAGTG-3';
```

Figure 10:
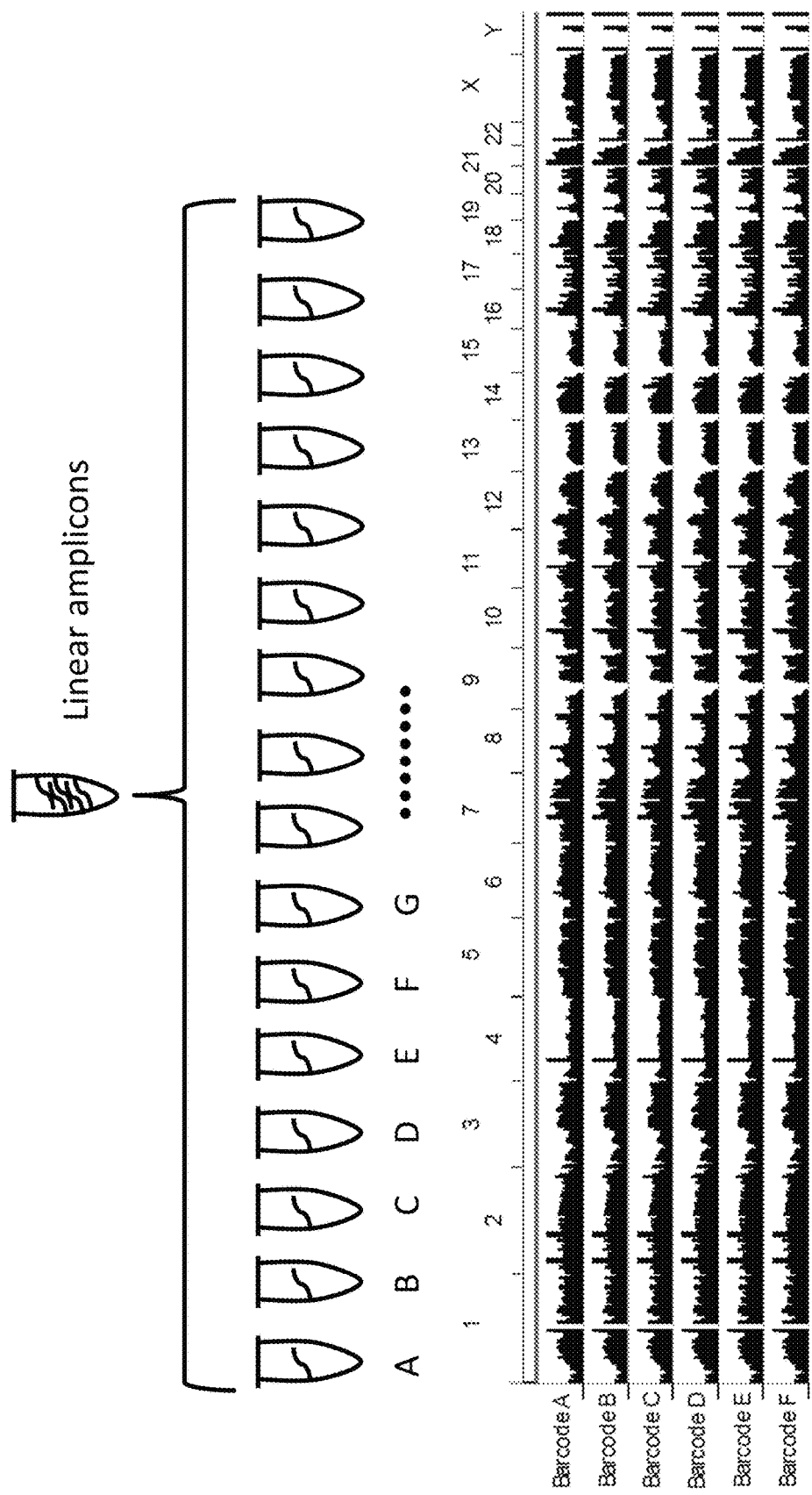
FIG. 10: The diagram illustrates examples of procedures following the linear amplification. Linearly produced DNA semiamplicons or full amplicons are divided into multiple tubes. So the independent linear copies will be amplified in different tubes. The sequencing libraries are constructed using the amplified DNA from each tube respectively and sequenced on a next-generation sequencer. The bottom panel shows one snapshot of the sequencing data. One can see the similarly even coverage across the chromosomes. The data include six libraries constructed from the six of sixteen tubes that the linearly amplified amplicons are divided into.

The amplification buffer can be split into multiple tubes. The linearly amplified products will be split into each tube (FIG. 10). Amplification is performed with standard PCR procedures as follows to generate 1-2 μg of DNA material.
94° C.—20 seconds
58° C.—20 seconds
65° C.—1 minutes
72° C.—1 minutes
Repeat the above cycle 20×
72° C.—5 minutes
4° C.—∞

After the second round of amplification, DNA can be purified using a Qiagen column and stored for a next procedure to remove the primer end of the DNA amplicons.

Figure 11:
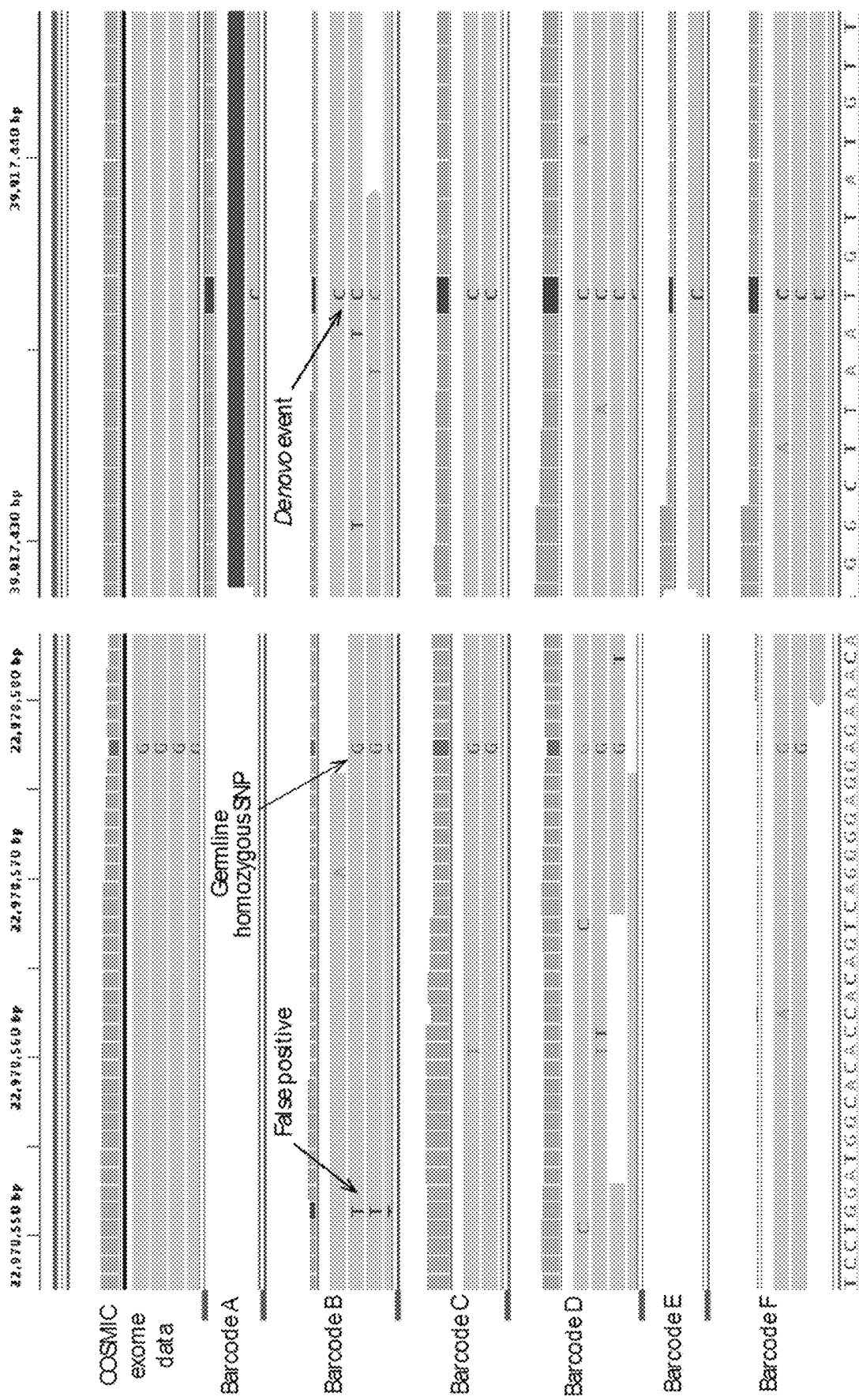
FIG. 11: The next generation sequencing result demonstrates that the linear amplification allows the detection of germline/somatic mutations and identification of amplification errors The plot shows the reads from the sequencing experiment described in FIG. 10. The typical patterns of the reads for both true mutations and false positives are indicated in the plot. The mutation in the right panel shows the detection of a de novo mutation in the cell that was sequenced comparing to the existing database.

The amplicon products can be used for whole genome or targeted (e.g., exome and any list of gene panels) sequencing/resequencing and genotyping methods including Sanger sequencing, next-generation sequencing and microarray, etc. A result of next-generation sequencing is shown in FIG. 10 and FIG. 11.

Example 3

Whole Genome Single Fragment Amplification in Micro-Droplets/Wells

Figure 6:
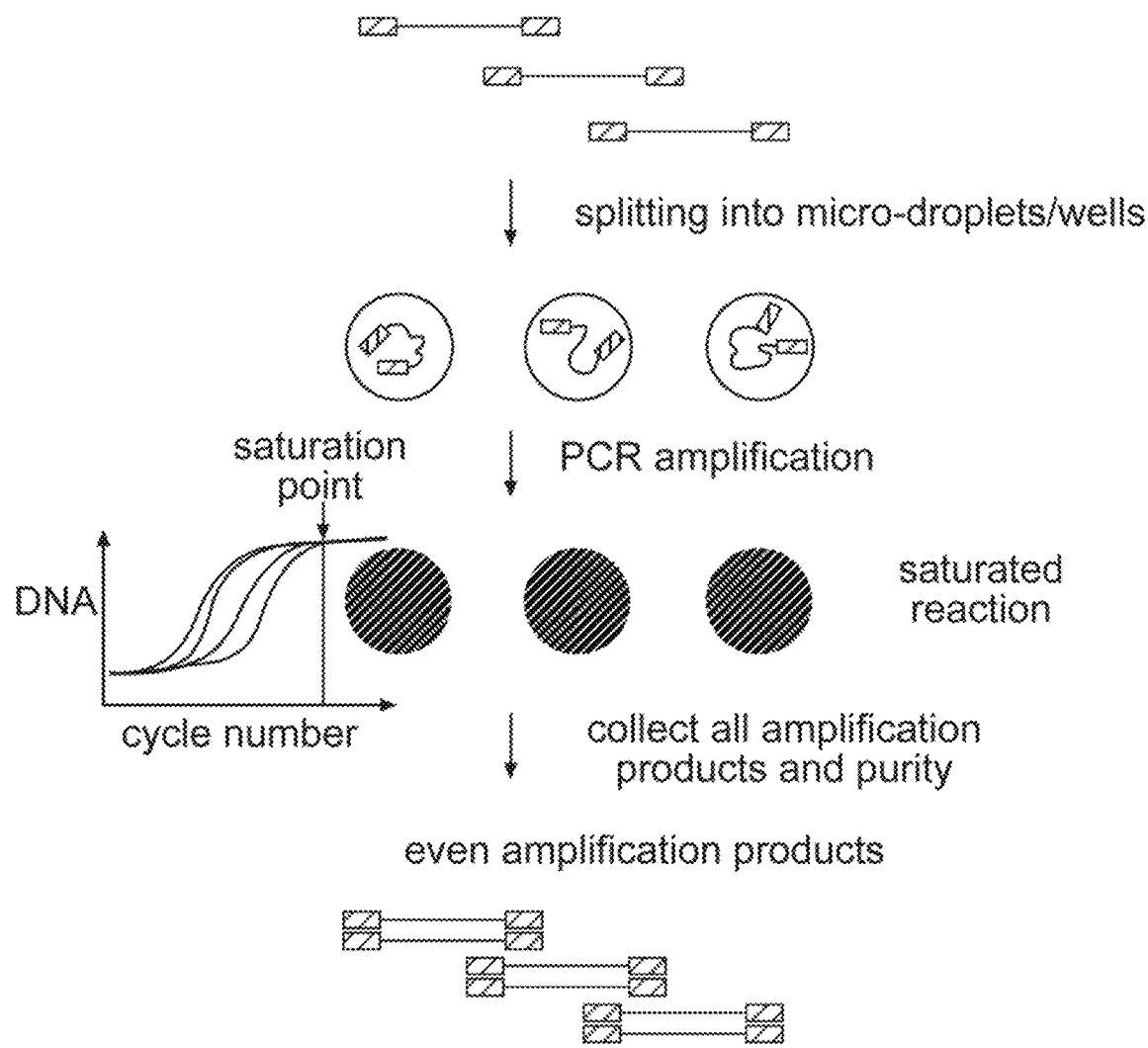
FIG. 6 provides an example of whole genome amplification in microdroplets or wells.

Linearly amplified amplicons from EXAMPLE 1 cover the whole genome of the single cell DNA and can be used as the starting materials for the following procedure (see FIG. 6).

Additional methods of amplification known to those of skill in the art can be used as follows.

The product is split into tens of millions of picoliter micro-droplets/wells or femtoliter micro-droplets/wells. Commercial available microfluidic based droplet emulsifiers or microfluidic devices with picoliter or femtoliter microwells can be used. By reaching to saturation of the amplification (limited either by available primers or dNTPs) in each reaction micro-droplet/well, the individual DNA fragments are amplified to similar level.

Additional methods of creating large scale of individual reactions known to those of skill in the art can be used as follows.

PCR reactions can be performed for amplifying single amplicons in each of 10 millions of micro-droplets/wells.
94° C.—20 seconds
58° C.—20 seconds
65° C.—1 minutes
72° C.—1 minutes
Repeat the above cycle 20×
72° C.—5 minutes
4° C.—∞

The DNA products from each micro-droplets/wells are collected and purified using commercial purification column or ethanol precipitations.

Example 4

Removing Primer Sequence in Amplicons

Figure 7:
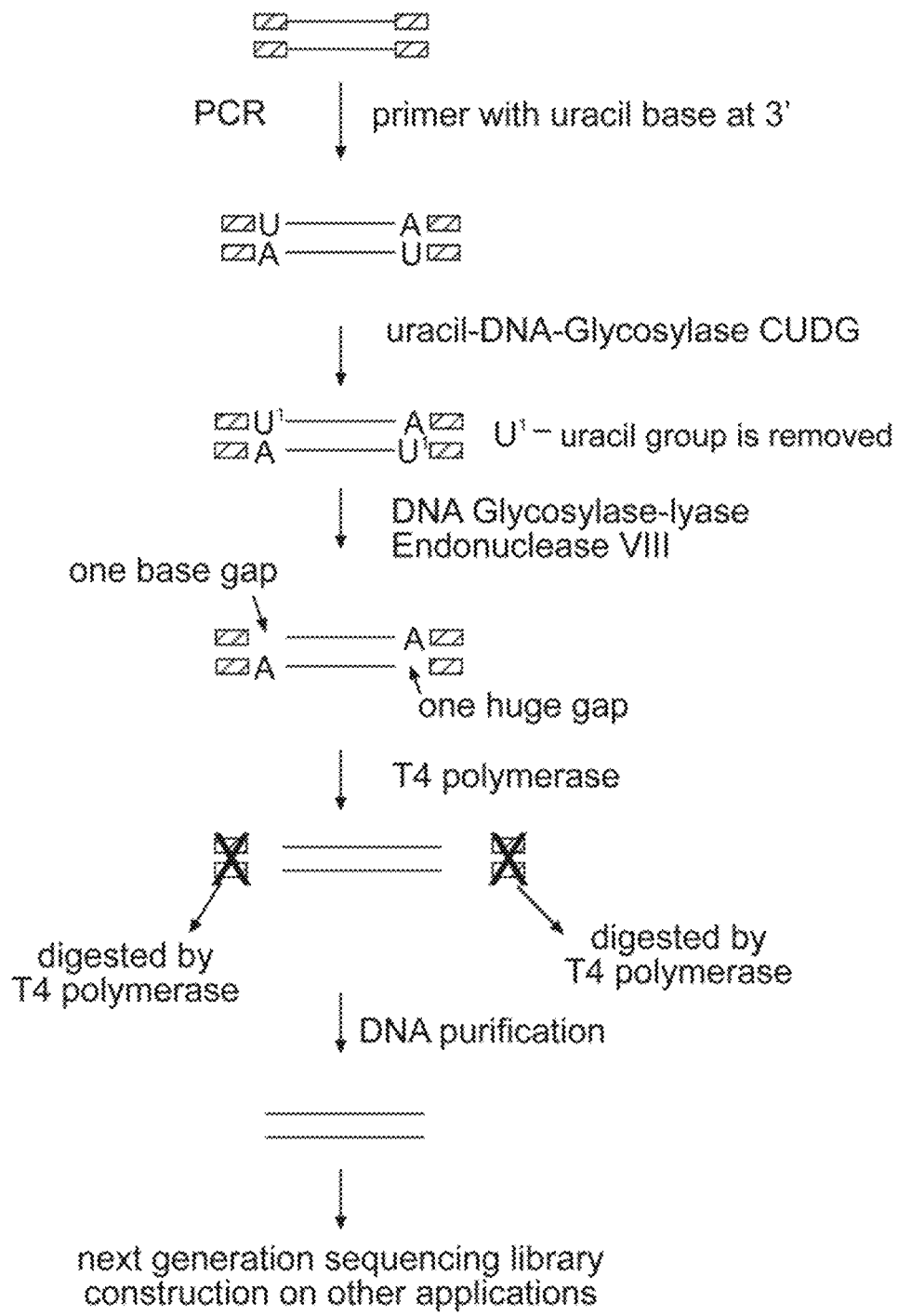
FIG. 7 demonstrates removal of primer sequence in primers utilizing particular enzymes.

The fully amplified DNA collected from Example II can be reamplified for 6 cycles with the following uracil primer (see, for example, FIG. 7):

```
                                          (SEQ ID NO: 3)
5'-GTGAGTGATGGTTGAGGATGAGTGGU-3'
```

After the amplification, DNA product is purified using DNA purification column. Mixture enzymes of Uracil-DNA-Glycosylase (UDG) and DNA glycosylase-lyase Endonuclease VIII is used to remove the U base in the primer sequence. UDG catalyzes the excision of uracil group and Endonuclease VIII will remove apyrimidinic base.

The gapped DNA is purified using DNA purification column. S1 nuclease with Zn++ ion as catalytic ion cut through the single strand DNA at the nicking site. As a result, the original primer sequence is removed on both end of DNA.

T4 polymerase can also be used for removing primer sequencing. The enzyme will find the gap and digest from 3' to 5' from the gap site. After removing the top strand, the enzyme will remove the 3' overhang, i.e. the bottom strand.

The DNA product is purified using DNA purification column. The DNA will can be used directly in the library construction for next generation sequencing experiment.

Example 5

PCR Amplification of Single Cell's DNA Fragments Separately in Large Number of Micro-Droplets/Wells PCR amplicons covering the whole genome of the single cell DNA can be used as the starting materials.

Additional methods of amplification known to those of skill in the art can be used as follows.

The product is split into tens of millions of picoliter micro-droplets/wells or femtoliter micro-droplets/wells. Commercial available microfluidic based droplet emulsifiers or microfluidic devices with picoliter or femtoliter microwells can be used. By reaching to saturation of the amplification (limited either by available primers or dNTPs) in each reaction micro-droplet/well, the individual DNA fragments are amplified to similar level.

PCR reactions can be performed for amplifying single amplicons in each of 10 millions of micro-droplets/wells.

94° C.—20 seconds
58° C.—20 seconds
65° C.—1 minutes
72° C.—1 minutes
Repeat the above cycle 20×
72° C.—5 minutes
4° C.—∞

The DNA products from each micro-droplets/wells are collected and purified using commercial purification column or ethanol precipitations.

Example 6

SDA of Single Cell's DNA Fragments Separately in Large Number of Micro-Droplets/Wells Strand Displacement Amplification (SDA) is used to create individual fragments. However, the amplification time is minimized 10 to 30 minutes comparing to normal SDA reaction. This will avoid the formation of hyper-branches and the amplification bias caused by hyper-branched single strand DNA.

The new displacement enzyme (Phi29) is added and the reaction is split into 10 millions picoliter micro-droplets/wells or femtoliter micro-droplets/wells. Commercial available microfluidic based droplet emulsifiers or microfluidic devices with picoliter or femtoliter microwells can be used. Strand Displacement Amplification (SDA) can be resumed at 30 degree to amplify single DNA fragments in each micro-droplets/wells. Majority of individual micro-droplets/wells have none or limited number of DNA fragment. The SDA is performed for extended time (12 hours) to reach the saturation.

By amplifying the individual fragments in separated wells, the reaction avoids fragment interference and competition. By reaching to saturation of the amplification (limited either by available primers or dNTPs) in each reaction micro-droplet/well, the individual DNA fragments are amplified to similar level.

The DNA products from each micro-droplets/wells are collected and purified using commercial purification column or ethanol precipitations.

Additional methods of amplification known to those of skill in the art can be used as follows. Additional methods of creating large scale of individual reactions known to those of skill in the art can be used as described herein.

Example 7

PCR Amplification of Single Cell's RNA Fragments Separately in Large Number of Micro-Droplets/Wells cDNA generated by reverse transcription of the single cell RNA transcripts can be used as the starting materials.

Additional methods of amplification known to those of skill in the art can be used as follows.

The product is split into tens of millions of picoliter micro-droplets/wells or femtoliter micro-droplets/wells. Commercial available microfluidic based droplet emulsifiers or microfluidic devices with picoliter or femtoliter microwells can be used. By reaching to saturation of the amplification (limited either by available primers or dNTPs) in each reaction micro-droplet/well, the individual DNA fragments are amplified to similar level.

PCR reactions can be performed for amplifying single amplicons in each of 10 millions of micro-droplets/wells.

94° C.—20 seconds
58° C.—20 seconds
65° C.—1 minutes
72° C.—1 minutes
Repeat the above cycle 20×
72° C.—5 minutes
4° C.—∞

The DNA products from each micro-droplets/wells are collected and purified using commercial purification column or ethanol precipitations.

Example 8

Methods for Human Cancer Samples

One can utilize methods and compositions of the present embodiments for characterizing the complex evolution of tumorigenesis. Compared to large scale sequencing endeavors of solid cancers, one can push the frontier of sequencing studies toward the earliest stage of tumors that one can retrieve in a clinical setting, for example. This only becomes plausible with the single cell whole-genome amplification assay that allows accurate SNV calling as described above and an efficient single cell isolation assay working with clinical samples.

Single Cell Isolation from Clinical Tissue Sample

In order to apply the novel single cell analysis to clinical samples, one can utilize an effective method to isolate the cell of interest. One can obtain single cell suspensions from tissue samples by enzymatic dissociation, for example. However, one would lose the proximity information of the dissociated cells. The alternative method that can allow obtaining morphological information is microscopic laser-dissection. However, as useful as the laser micro-dissection is, it cannot guarantee that a complete single cell will be retrieved. To obtain complete cells from the tissue structure of interest, one can combine both assays in the studies. One can prepare 100-micron thick tissue section and cut single tissue unit (i.e., individual gland, ducts, etc.) out of this section. By doing this, one can guarantee that there are intact single cells in the dissected tissue. Next one can apply enzymatic disassociation. This whole digestion process can be recorded by bright field microscopy imaging.

Genome Heterogeneity in Early Tumor Development

It is Probably not Surprising that One Cell in an Organ Randomly Undergoes a driver mutation, considering there are thousands of cells in the tissue. Following the first driver mutation, it will be extremely rare for this cell to acquire a second driver mutation, considering the pool of three billion bases of the genome. In reality, after acquiring the first driver mutation (Kras in PanIN), the cell can escape from the normal differentiation and start to proliferate and reprogram. Following the expansion, this abnormal group of precursor cells could come across internal and external crisis, e.g. telomere crisis, immune attack and hypoxia. As a result, one can anticipate increased cell death and decelerated proliferation. This stage of existence can be represented by dysplasia and it could be the critical stage of cancer development. Dysplasia can survive for years and accumulate high degree of genome heterogeneity.

Figure 8:
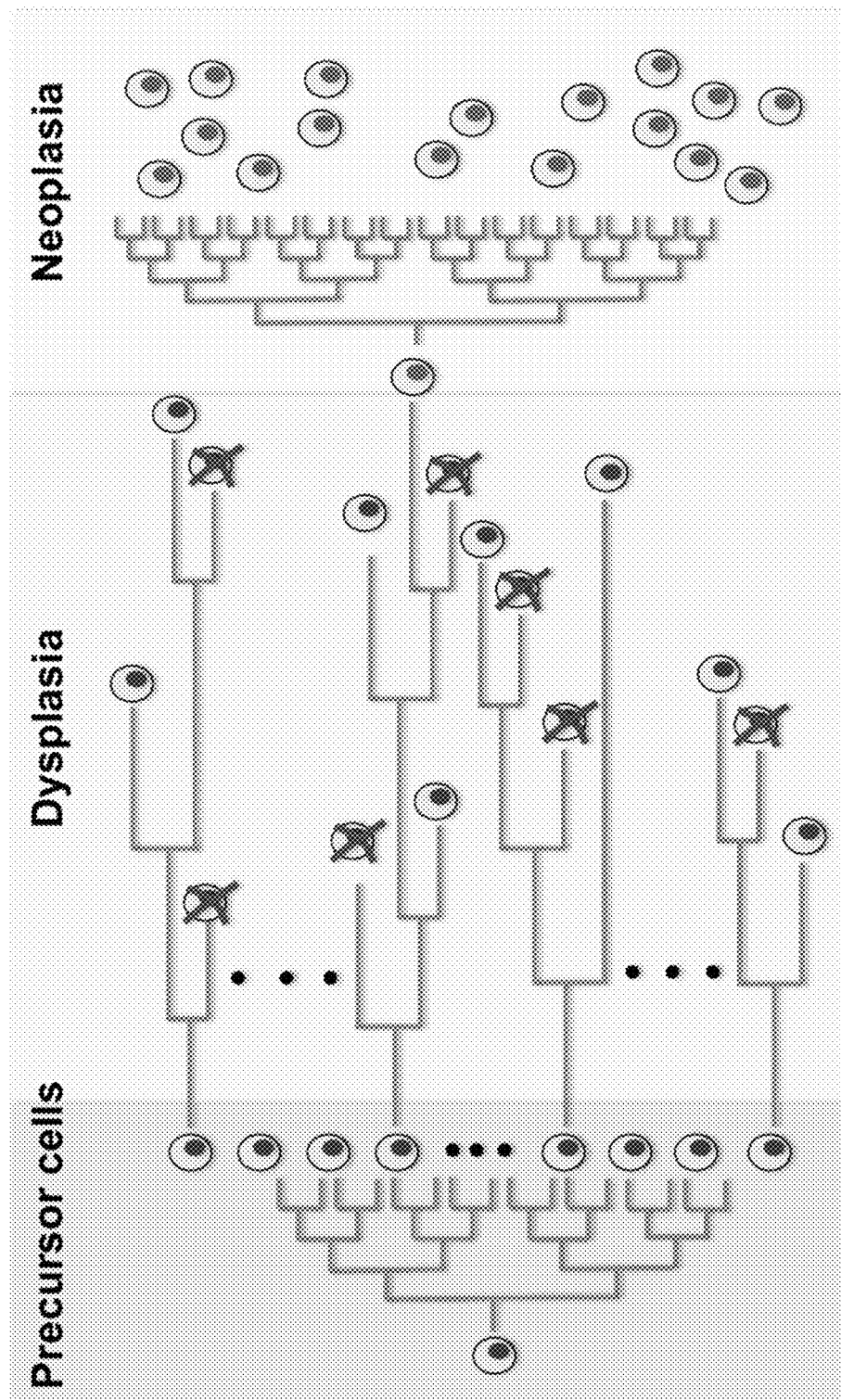
FIG. 8: Overview of the early tumor development. In precursors, one can expect limited number of mutations. In dysplasia, one can expect that the cells accumulate a significant number of mutations and high degree of genome heterogeneity comparing to neoplasia.

With whole-genome sequencing of tumors, tumor cells usually accumulate between 1,000 and 10,000 somatic mutations across various types of adult cancer (Stratton, 2011). This number sets the range for the number of mutations necessary for the precursor cell to develop into a cancer. So, one expects that hundreds to thousands of mutations accumulate during the latent period of dysplastic cells. The argument is that only when extensive mutations have been acquired by a large number of precursor cells, can one of the cells undergo the next important driver mutation. Once this occurs, one anticipates that this cell will gain significant proliferative advantage compared to the others and lead to a much bigger clonal expansion; this stage of proliferation will correspond to the stage of neoplasia (FIG. 8). With various types of crises, there may be multiple stages of dysplasia and neoplasia as well as the coexistence of them in one tumor. However, as cell populations become larger and larger, the clonal evolution will speed up and eventually lead to malignant transformation.

With the picture described above for early cancer development, we expect to see high degree of genome heterogeneity at the dysplasia stage. There may be less heterogeneity among neoplastic cells. By comparing the mutations between dysplasia and neoplasia, we could uncover the potential mutations that lead to this transformation.

In the case of pancreatic adenocarcinoma, Kras, p16, p53 and SMAD4 are essentially the most significant driver mutations. It is generally believed that the Kras mutation is the first driver mutation as it occurs in over 90% of pancreatic carcinomas. Even low-grade PanIN-1A lesions harbor the Kras mutation. When the neoplastic nature has not been unambiguously established, it is designated PanIN/L-1A. This grade corresponds to the earliest PanIN lesion that we can capture in clinical samples. With the paucity of cells, single cell whole-genome sequencing can be used to unveil the genome heterogeneity in low grade PanIN/L-1A. From PanIN-1A to the PanIN-2 stage, other critical mutations, e.g. p16, p53 or SMAD4 could be acquired, and we anticipate the development of neoplasia.

The early stage of genome heterogeneity will also include aneuploidy due to telomere crisis or other stresses. The chromosomal abnormalities have been widely observed in colorectal and breast adenomas. By duplicating or deleting large chromosomal fragments, aneuploidy could lead to cell death, or alternatively stress cell towards reprogramming. It is evident that aneuploidy will influence the evolutionary dynamics, and it could also play a driving role leading to malignant transformation if the deletions happen in the regions with critical tumor suppressor genes. Whether aneuploidy plays a driver role to lead to neoplasia or simply a supporting role to increase the survival of dysplasia cells will be addressed in this study.

REFERENCES

Cheng J, Vanneste E, Konings P, Voet T, Vermeesch J R, Moreau Y. Single-cell copy number variation detection. Genome biology. 2011; 12(8):R80. doi: 10.1186/gb-2011-12-8-r80. PubMed PMID: 21854607; PubMed Central PMCID: PMC3245619.

Dean F B, Hosono S, Fang L, Wu X, Faruqi A F, Bray-Ward P, et al. Comprehensive human genome amplification using multiple displacement amplification. Proceedings of the National Academy of Sciences. 2002; 99(8):5261-6. doi: 10.1073/pnas.082089499.

Dean F B, Nelson J R, Giesler T L, Lasken R S. Rapid Amplification of Plasmid and Phage DNA Using Phi29 DNA Polymerase and Multiply-Primed Rolling Circle Amplification. Genome Res. 2001; 11(6):1095-9. doi: 10.1101/gr.180501.

Fan H C, Wang J, Potanina A, Quake S R. Whole-genome molecular haplotyping of single cells. Nature biotechnology. 2011; 29(1):51-7. doi: 10.1038/nbt.1739. PubMed PMID: 21170043.

Hou Y, Song L, Zhu P, Zhang B, Tao Y, Xu X, et al. Single-cell exome sequencing and monoclonal evolution of a JAK2-negative myeloproliferative neoplasm. Cell. 2012; 148(5):873-85.doi:10.1016/j.cell.2012.02.028. PubMed PMID: 22385957.

Lao K, Xu N, Straus N. Whole genome amplification using single-primer PCR. Biotechnol Journal. 2008; 3(3):378.

Navin N, Kendall J, Troge J, Andrews P, Rodgers L, McIndoo J, et al. Tumour evolution inferred by single cell sequencing. Nature. 2011; 472(7341):90-4. doi: 10.1038/nature09807. PubMed PMID: 21399628.

Stratton M R. Exploring the genomes of cancer cells: progress and promise. Science. 2011; 331(6024):1553-8. doi: 10.1126/science.1204040. PubMed PMID: 21436442.

Telenius H, Carter N P, Bebb C E, Nordenskjold M, Ponder B A, Tunnacliffe A. Degenerate oligonucleotide-primed PCR: general amplification of target DNA by a single degenerate primer. Genomics. 1992; 13(3):718-25. PubMed PMID: 1639399.

Zhang K, Martiny A C, Reppas N B, Barry K W, Malek J, Chisholm S W, et al. Sequencing genomes from single cells by polymerase cloning. Nature biotechnology. 2006; 24(6):680-6. doi: 10.1038/nbt1214. PubMed PMID: 16732271.

Zhang L, Cui X, Schmitt K, Hubert R, Navidi W, Arnheim N. Whole genome amplification from a single cell:implications for genetic analysis. Proceedings of the National Academy of Sciences of the United States of America. 1992; 89(13):5847-51. PubMed PMID: 1631067; PubMed Central PMCID: PMC49394.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of analyzing nucleic acid of one or more cells from a sample from an individual, comprising the steps of:
providing or obtaining a sample comprising one or more cells from:
(a) a pregnant mother, wherein the sample is blood or amniotic fluid; or
(b) an individual that has cancer or is suspected of having cancer or is being monitored for cancer therapy outcome, wherein the sample is blood, urine, biopsy, fecal matter, nipple aspirate, or cheek scrapings;
exposing nucleic acid from the one or more cells to a first plurality of primers and to a polymerase that comprises strand displacement activity, wherein the primers anneal to the nucleic acid and the primers are extended by the polymerase, wherein the primers comprise a restriction endonuclease site, thereby producing a mixture comprising primer-annealed nucleic acid templates;

exposing the primer-annealed nucleic acid templates to two or more of extension, melting, and annealing steps, thereby producing a first mixture of nucleic acid template, linearly produced semi-amplicons, and nonlinearly produced full amplicons;

annealing and extension of the first plurality of primers or a second plurality of primers to the mixture, wherein said annealing and extension occurs with no melting of the nucleic acids, to produce a second mixture comprising nucleic acid template, linearly produced single-stranded semi-amplicons, looped full amplicons, and double stranded nonlinearly produced full amplicons;

exposing the second mixture to the restriction endonuclease corresponding to the restriction endonuclease site of the primers, thereby rendering the digested double stranded nonlinearly produced full amplicons and the digested looped full amplicons unable to be annealed to by the first plurality of primers or the second plurality of primers;

exposing the nucleic acid template and linearly produced single-stranded semi-amplicons to further extension, melting, and annealing steps, thereby producing linearly produced full amplicons; and analyzing part or all of a sequence in the linearly produced full amplicons.

2. The method of claim 1, further comprising the step of subjecting the linearly produced full amplicons to amplification.

3. The method of claim 1, wherein the polymerase lacks exonuclease activity.

4. The method of claim 1, wherein the primers in the first plurality, second plurality, or both comprise the following formula:

$$X_n Y_m Z_p,$$

wherein n is greater than 2 and X is 40%-60% G-rich or 40%-60% C-rich, wherein Y is any nucleotide and m is 3-8 nucleotides and wherein Z is a G when $X_n$ is G-rich or is C when $X_n$ is C-rich, wherein p is 2-4 nucleotides.

5. The method of claim 1, wherein the extension step of the primer-annealed nucleic acid templates occurs at a temperature range of from 30° C. to 65° C.

6. The method of claim 1, wherein at least the majority of the linearly produced full amplicons are separated from each other.

7. The method of claim 1, wherein at least the majority of the linearly produced full amplicons are each placed in separate containers.

8. The method of claim 7, wherein the separately contained amplicons are subjected to amplification.

9. The method of claim 1, wherein the linearly produced full amplicons are subjected to a mixture of uracil-DNA-glycosylase and DNA glycosylase-lyase endonuclease VIII, followed by being subjected to S1 nuclease or T4 polymerase.

10. The method of claim 1, wherein the linearly produced full amplicons are subjected to library construction methods.

11. The method of claim 1, wherein one or more of the linearly produced full amplicons is assayed for a specific nucleotide or nucleotide sequence.

12. The method of claim 1, wherein the level of expression of nucleic acids in cells in the sample from the individual is represented in the number of linearly produced full amplicons.

13. The method of claim 1, wherein the nucleic acid is from a genome or transcriptome of the cell.

* * * * *

SEQUENCE LISTING

```
<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (27)..(31)
<223> OTHER INFORMATION: n is a, c, g, or t

<400> SEQUENCE: 1
gtgagtgatg gttgaggatg agtggtnnnn nggg                            34

<210> SEQ ID NO 2
<211> LENGTH: 34
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (27)..(31)
<223> OTHER INFORMATION: n is a, c, g, or t

<400> SEQUENCE: 2
gtgagtgatg gttgaggatg agtggtnnnn nttt                            34

<210> SEQ ID NO 3
<211> LENGTH: 26
<212> TYPE: DNA
<213> ORGANISM: Artificial Sequence
<220> FEATURE:
<223> OTHER INFORMATION: Synthetic Primer

<400> SEQUENCE: 3
gtgagtgatg gttgaggatg agtggu                                     26

<210> SEQ ID NO 4
<211> LENGTH: 26
<212> TYPE: DNA
<213> ORGANISM: Artificial Sequence
<220> FEATURE:
<223> OTHER INFORMATION: Synthetic Primer

<400> SEQUENCE: 4
gtgagtgatg gttgaggatg agtggt                                     26

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer

<400> SEQUENCE: 5
gtgagtgatg gttgaggatg agtg                                       24
```